(12) United States Patent
Biscup

(10) Patent No.: US 7,172,594 B2
(45) Date of Patent: Feb. 6, 2007

(54) ELECTRO-STIMULATION AND MEDICAL DELIVERY DEVICE

(75) Inventor: Robert S. Biscup, Chagrin Falls, OH (US)

(73) Assignee: Spineco, Inc., Westlake, OH (US)

( * ) Notice: Subject to any disclaimer, the term of this patent is extended or adjusted under 35 U.S.C. 154(b) by 0 days.

(21) Appl. No.: 10/818,736

(22) Filed: Apr. 6, 2004

(65) Prior Publication Data
US 2004/0193166 A1   Sep. 30, 2004

Related U.S. Application Data

(62) Division of application No. 10/269,601, filed on Oct. 11, 2002, now abandoned.

(51) Int. Cl.
*A61B 17/58* (2006.01)

(52) U.S. Cl. ...................................................... 606/73

(58) Field of Classification Search ............ 606/61–62, 606/69–77; 623/17; 600/9, 13, 15, 424; 607/50–52, 116–117, 149
See application file for complete search history.

(56) References Cited

U.S. PATENT DOCUMENTS

| | | | | |
|---|---|---|---|---|
| 3,918,440 A | * | 11/1975 | Kraus | ............................ 602/2 |
| 4,027,392 A | * | 6/1977 | Sawyer et al. | ............... 433/174 |
| 4,306,564 A | * | 12/1981 | Kraus | ........................... 607/51 |
| 4,351,337 A | | 9/1982 | Sidman | |
| 4,359,318 A | * | 11/1982 | Gittleman | .................. 433/173 |
| 4,523,910 A | | 6/1985 | Makovich | |
| 4,653,489 A | | 3/1987 | Tronzo | |
| 4,701,180 A | | 10/1987 | Kelly et al. | |
| 4,781,591 A | * | 11/1988 | Allen | .......................... 433/174 |
| 4,877,019 A | * | 10/1989 | Vives | .......................... 606/64 |
| 4,886,074 A | * | 12/1989 | Bisping | ..................... 607/116 |
| 5,292,252 A | * | 3/1994 | Nickerson et al. | ........... 433/173 |
| 5,562,670 A | * | 10/1996 | Brånemark | ................... 606/73 |
| 5,571,139 A | * | 11/1996 | Jenkins, Jr. | .................. 606/232 |
| 5,584,688 A | | 12/1996 | Sakuma et al. | |
| 5,725,377 A | * | 3/1998 | Lemler et al. | ............... 433/173 |
| 5,836,935 A | | 11/1998 | Ashton et al. | |
| 5,882,350 A | | 3/1999 | Ralph et al. | |
| 5,968,098 A | | 10/1999 | Winslow | |
| 5,989,254 A | | 11/1999 | Katz | |
| 5,997,539 A | | 12/1999 | Errico et al. | |
| 6,004,322 A | | 12/1999 | Bernstein | |
| 6,005,349 A | | 12/1999 | Jackson | |
| 6,017,344 A | | 1/2000 | Errico et al. | |
| 6,034,295 A | * | 3/2000 | Rehberg et al. | ........... 623/23.49 |
| 6,053,917 A | | 4/2000 | Sherman et al. | |
| 6,056,753 A | | 5/2000 | Jackson | |
| 6,083,227 A | | 7/2000 | Saurat et al. | |
| 6,113,601 A | | 9/2000 | Tatar | |
| 6,120,502 A | * | 9/2000 | Michelson | .................... 606/61 |
| 6,183,472 B1 | | 2/2001 | Lutz | |

(Continued)

*Primary Examiner*—Eduardo C. Robert
*Assistant Examiner*—Annette Reimers
(74) *Attorney, Agent, or Firm*—Fay Sharpe Fagan Minnich & McKee; Brian E. Turung

(57) ABSTRACT

A pedicle screw for at least partial insertion into a bone and/or cartilage. The pedicle screw includes a head and a lower portion connected to the head. The lower portion includes at least one interface that designed to at least partially discharge an electrical current, and/or a medical substance to or adjacent to the bone and/or cartilage.

98 Claims, 9 Drawing Sheets

U.S. PATENT DOCUMENTS

| | | |
|---|---|---|
| 6,224,596 B1 | 5/2001 | Jackson |
| 6,319,254 B1 | 11/2001 | Giet et al. |
| 6,340,588 B1 | 1/2002 | Nova et al. |
| 6,368,319 B1 | 4/2002 | Schaefer |
| 6,375,657 B1 | 4/2002 | Doubler et al. |
| 6,402,752 B2 | 6/2002 | Schläffler-Wachter et al. |
| 6,554,830 B1 | 4/2003 | Chappius |
| 6,565,572 B2 | 5/2003 | Chappius |
| 6,654,629 B2 * | 11/2003 | Montegrande ............... 600/424 |
| 6,778,861 B1 * | 8/2004 | Liebrecht et al. ........... 607/116 |
| 2001/0007074 A1 | 7/2001 | Strobel et al. |
| 2001/0053913 A1 | 12/2001 | Freedland |
| 2002/0029043 A1 * | 3/2002 | Ahrens et al. ................ 606/73 |
| 2002/0049394 A1 * | 4/2002 | Roy et al. .................... 600/594 |
| 2002/0095187 A1 * | 7/2002 | Thompson et al. ............. 607/9 |

* cited by examiner

ELECTRO-STIMULATION AND MEDICAL DELIVERY DEVICE

The present invention is a divisional of U.S. patent application Ser. No. 10/269,601 filed Oct. 11, 2002 now abandoned.

The present invention pertains to prosthetic implants, and more particularly to pedicle screws, nails or posts that can be inserted into bone and/or cartilage.

BACKGROUND OF THE INVENTION

The human spine is made up of a column of thirty-three bones and their adjoining structures. The bodies of these vertebrae are connected by anterior and posterior ligaments and by discs of fibrocartilage generally known as intervertebral discs. These discs are positioned between opposite faces of adjacent vertebral bodies. This column of vertebrae and intervertebral discs form a central axis that supports the head and torso. These vertebrae also enclose an opening through which the spinal cord passes.

The presaccral vertebrae are normally held in position to one another by the intervertebral discs, ligaments and musculature of the body. These vertebrae move relative to adjacent vertebrae thus permitting the head to be turned relative the body and providing a wide range of flexibility to the spine.

One of the most costly health problems in society involves back pain and pathology of the spine. These problems can affect individuals of all ages and can result in great suffering to victims. Back pain can be caused by several factors such as congenital deformities, traumatic injuries, degenerative changes to the spine, and the like. Such changes can cause painful excessive motion, or collapse of a motion segment resulting in the contraction of the spinal canal and compression of the neural structures, causing debilitating pain, paralysis or both, which in turn can result in nerve root compression or spinal stenosis.

Nerve conduction disorders can also be associated with intervertebral discs or the vertebrae themselves. One such condition is herniation of the intervertebral disc, in which a small amount of tissue protrudes from the sides of the disc into the foramen to compress the spinal cord. A second common condition involves the development of small bone spurs, termed osteophytes, along the posterior surface of the vertebral body, again impinging on the spinal cord.

Upon identification of these abnormalities, surgery may be required to correct the problem. For those problems associated with the formation of osteophytes or herniations of the intervertebral disc, one such surgical procedure is intervertebral discectomy. In this procedure, the involved vertebrae are exposed and the intervertebral disc is removed, thus removing the offending tissue or providing access for the removal of the bone osteophytes. A second procedure, termed a spinal fusion, may then be required to fix the vertebrae together to prevent movement and maintain a space originally occupied by the intervertebral disc. Although this procedure may result in some minor loss and flexibility in the spine, due to the relatively large number of vertebrae, the minor loss of mobility is typically acceptable.

For the replacement of vertebra of the human spinal column, for the distraction of the spinal column, for the stabilization of the vertebrae and likewise, it is known to apply pedicle screws. The pedicle screw is screwed into the pedicle of the vertebra and the head of the pedicle screw is connected to suitable provisions, for example to a stabilizing system, to distraction rods, etc. During the treatment of the spine, the pedicle screw is generally first rotated into the pedicle. Subsequently, the insertion of the rod is effected.

A standard pedicle screw assembly comprises a screw having an externally threaded stem having in turn a head provided with parts allowing it to be secured to one end of a distraction rod. Typically two such pedicle screws are inserted into respective vertebrae and are secured to a rod to distract and/or stabilize a spinal column after, for instance, a disk operation. One commonly used pedicle screw is disclosed in German Patent No. 4,107,480, which is incorporated herein by reference, and includes a head that has a pair of outwardly projecting parallel ridges with overhanging inner edges. A cap formed with a pair of complementary inwardly open slots fit with these ridges. The pedicle screw is threaded into the vertebrae, an end of the rod is fitted to its outer end, the cap is then slid transverse to the pedicle screw axis and parallel to the rod over the rod to capture it, and finally a cap screw threaded into the cap and tightened to press the rod down against the head of the pedicle screw and thereby fix the rod, cap, and screw together. Many other pedicle screw designs have been developed to simplify the insertion of the pedicle screw into the pedicle, and/or to reduce damage to the pedicle screw and/or the pedicle during surgery. Some of these pedicle screw designs are disclosed in U.S. Pat. Nos. 5,882,350; 5,989,254; 5,997,539; 6,004,322; 6,004,349; 6,017,344; 6,053,917; 6,056,753; 6,083,227; 6,113,601; 6,183,472; 6,224,596; 6,368,319; 6,375,657; and 6,402,752; and the patents cited and disclosed in such patents. All these designs of pedicle screws are incorporated herein by reference.

After the pedicle screw is inserted in the pedicle, the bone around the pedicle screw must heal to properly secure the pedicle screw in the bone. Any infection that occurs around the pedicle screw can slow the healing process and/or damage the bone around the pedicle screw thereby weakening the connection between the bone and pedicle screw. Typically, a patient is given antibiotics for several days after the surgery to reduce the occurrence of infection about the pedicle screw. The patient may also receive electrical stimulation during surgery to promote the healing process of the bone about the pedicle screw. Both of these techniques have improved the post-operative success of the surgical procedure; however, improved success rates are still needed.

In view of the present state of technology related to prosthetic implants, there is a continued need for pedicle screws that reduce the occurrence of post-operative failure due to infection and/or improper healing about the pedicle screw.

SUMMARY OF THE INVENTION

The present invention pertains to an improved implant, and more particularly to an improved connector such as, but not limited to, a screw, nail or post which promotes healing about the screw, nail or post, and even more particularly to an improved pedicle screw, nail or post which promotes healing about the screw, nail or post.

In accordance with the principal feature of the present invention, there is provided an improved screw, nail or post used for insertion into bone and/or cartilage. The screw, nail or post is generally used to anchor and/or affix an implant (e.g., rod, cage, stabilization system, etc.) to the bone and/or cartilage; however, the screw, nail or post can be used for other uses such as, but not limited to, attachment of ligaments; connecting and/or repairing broken bones; reducing pain; stabilizing a tissue ligaments, cartilage, and/or bone; an adjunct for another surgical procedure and the like. In one embodiment of the present invention, the screw, nail or post is used to repair a spinal column. During the replacement of vertebra of the human and/or animal spinal column, the distraction of the spinal column, and/or the stabilization of the spinal column, pedicle screws, nails, and/or posts of the present invention can be used. Generally, the screw, nail, and/or post is inserted into the pedicle of the vertebra; however, the screw, nail or post can be connected to other regions of the vertebra. In still another and/or alternative embodiment of the invention, the screw, nail or post is used in areas of a body other than the spine. In one aspect of the embodiment, the screw, nail or post is used to connect together fractured or broken bones. The bone or bones are not limited to bones of the vertebra, but include any bone in which the screw, nail or post can be used to at least partially heal the bone. In another and/or alternative aspect of the embodiment, the screw, nail or post is used to connect ligaments together and/or to bone and/or cartilage. In still another and/or alternative aspect of the embodiment, the screw, nail or post is used to retain tissue (e.g., organs, muscle, etc.) in place. In yet another and/or alternative embodiment of the present invention, the screw, nail or post includes a head and a lower portion. In one aspect of this embodiment, the top surface of the head can have a number of different shapes (e.g., flat, sloped, acuate, circular, polygonal, etc.). In another and/or alternative aspect of this embodiment, the head can have a number of different surfaces (e.g., smooth, rough, ribbed, etc.). In still another and/or alternative aspect of this embodiment, the head can have a number of different shapes (e.g., spherical, ellipsoidal, cubic, orthogonic, etc.). In yet another and/or alternative aspect of this embodiment, the head can have a various side surfaces (e.g. ribs, grooves, slots, pits, etc.). In still yet another and/or alternative aspect of this embodiment, the head can include one or more openings. In still another and/or alternative aspect of this embodiment, the head can include one or more connectors. In a further and/or alternative aspect of this embodiment, the head can be rigidly connected to the lower portion or moveably connected to the lower portion. The shapes, surfaces, connectors, and/or openings of the head, and/or the type of connection between the head and lower portion a) facilitate in the insertion and/or removal of the screw, nail or post into bone and/or cartilage, b) facilitate in the attachment and/or disconnection of the head from other components of an implant (e.g., a stabilizing system, distraction rods, cage, mechanical and/or electrical mechanisms, insertion and/or removal tools, etc.), and/or c) facilitate in the operation of the implant and/or components connected to the screw, nail or post. In another and/or alternative embodiment of the invention, the lower portion of the screw includes a threaded outer surface. The nail or post may or may not have a threaded surface. In still another and/or alternative embodiment of the invention, the lower portion of the screw, nail or post can have a smooth surface, ribs, channels, barbs, teeth, etc. In yet another and/or alternative embodiment of the invention, the end of the lower portion of the screw, nail or post can be flat, sharp, forked, etc. In still yet another and/or alternative embodiment of the invention, the cross-sectional shape and/or area along the length of the lower portion can be constant or can vary. In one aspect of this embodiment, the cross-sectional shape and/or area along the length of the lower portion remains substantially constant. In another and/or alternative aspect of this embodiment, the cross-sectional shape and/or area along the length of the lower portion tapers along at least a portion of the lower portion. In a further and/or alternative embodiment of the invention, the lower portion can have a number of cross-sectional shapes (e.g. circular, polygonal, oval, arcuate, etc.). In still another and/or and/or alternative embodiment of the present invention, the head of the screw, nail or post can be designed to break off after inserting the lower portion into the bone and/or cartilage, and/or an implant. In still yet another and/or alternative embodiment of the present invention, lower portion of the screw, nail or post can include a feature (e.g., bore, notch, etc.) which facilitates subsequent removal of the lower portion from the location in which it is secured, and/or facilitate in the connection or more or more devices to the lower portion. In a further and/or alternative embodiment of the present invention, the lower portion can lie in a single axis or multiple axes. In one aspect of this embodiment, the one or more axes of the lower portion is fixed. In another and/or alternative aspect of this embodiment, the one or more axes of the lower portion can be altered. In essence, the screw, nail, or post has a configuration that suits the particular application of the screw, nail or post. In still further and/or alternative embodiment of the present invention, the screw, nail or post is designed to firmly secure one or more components of an implant to bone and/or cartilage to thereby reduce or prevent rotational or translational movement of one or more components of the implant. In yet a further and/or alternative embodiment of the present invention, the screw, nail or post is designed to be relatively small yet constructed to withstand sufficiently high torque and/or compressive forces to firmly set the screw, nail or post in the bone and/or cartilage. In still yet a further and/or alternative embodiment of the present invention, the screw, nail or post is designed to be easily manipulated to permit relatively rapid insertion and/or tightening during surgical procedures.

In another and/or alternative aspect of the invention, the screw, nail or post includes one or more cavities. The one or more cavities can be used for a variety of reasons such as, but not limited to, 1) weight distribution of the screw, nail or post; 2) structural integrity of the screw, nail or post (e.g., break points, flex points, compression points, etc.); 3) at least partially containing a substance such as, but not limited to, a material that a) promotes and/or inhibits bone and/or other tissue growth, b) inhibits rejection of the screw, nail or post, c) inhibits rejection of components connected to and/or located adjacent to the screw, nail or post, d) reduces infection, e) reduces inflammation, f) reduces pain, g) provides vitamins and/or minerals, h) provides genetic material, i) provides tissue, j) promotes healing of surrounding tissue, k) combats or cures cancer and/or other diseases, l) functions as a location and/or visual indicator, and/or the like; and/or 4) at least partially contains one or more electrical and/or mechanical components. In one embodiment of the present invention, the screw, nail or post includes a single cavity. In another and/or alterative embodiment of the present invention, the screw, nail or post includes a plurality of cavities. In one aspect of this embodiment, at least one cavity is separated from one other cavity. In another and/or alternative aspect of this embodiment, two or more cavities are connected together by one or more passageways. In still another and/or alternative embodiment of the present invention, at least one cavity has at least one access opening to the surface of the screw, nail or post. The access opening is generally designed to allow fluids and/or other material to flow into and/or out of the cavity. The size of the access is generally sized to regulate or control the fluid and/or material flow through the access opening. In yet another and/or alternative embodiment of the invention, the size of the one or more cavities is less than about 70% of the total volume of the screw, nail or post. In one aspect of this embodiment, the size of the one or more cavities is generally less than about 50% of the total volume of the screw, nail or post, typically less than about 40% of the total volume of the screw, nail or post, more typically less than about 30% of the total volume of the screw, nail or post, still more typically less than about 20% of the total volume of the screw, nail or post, and even more typically less than about 10% of the total volume of the screw, nail or post. In still yet another and/or alternative embodiment of the present invention, the shape of the one or more cavities is selected for a particular application of the one or more cavities. Any number of cavity shapes can be used (e.g., spherical, cylindrical, ovoid, pyramidal, cubical, orthogonic, etc.). Two or more cavities can have the same or different shape and/or volume. In a further and/or alternative embodiment of the present invention, the one or more cavities are located in the head of the screw, nail or post. In one aspect of this embodiment, at least a majority of the cavities and/or the majority of the volume of the cavities are located in the head. In still a further and/or alternative embodiment of the present invention, the one or more cavities are located in the lower portion of the screw, nail or post. In one aspect of this embodiment, at least a majority of the cavities and/or a majority of the volume of the cavities are located in the lower portion. In another and/or alternative aspect of this embodiment, the same number of cavities and/or the same volume of the cavities is located in the head and lower portion.

In still another and/or alternative aspect of the present invention, one or more substances are included on and/or in the screw, nail or post to improve the success of inserting the screw, nail, or post into the bone and/or cartilage, and/or to promote healing about the screw, nail or post. In one embodiment of the present invention, the substance includes, but is not limited to, antithrombogenic agents; steroids; thioprotese inhibitors; antimicrobials; antibiotics; tissue plasma activators; monoclonal antibodies; antifibrosis compounds; hormones; growth factors; anti-mitotic agents; immunosuppressive agents; sense or antisense oligonucleotides; nucleic acid analogues; inhibitors of transcription factor activity; anti-neoplastic compounds; chemotherapeutic compounds; radioactive agents; growth factors; antiplatlet compounds; antitabolite compounds; anti-inflammatory compounds; anticoagulent compounds; antimitotic compounds; antioxidants; antimetabolite compounds; anti-migratory agents; anti-matrix compounds; anti-vital compounds; anti-proliferatives; anti-fungal compounds; anti-protozoal compounds; human tissue; animal tissue; synthetic tissue; human cells, animal cells; synthetic cells; and/or bone-stimulation, bone-growth and/or bone-activating matter. In another and/or alternative embodiment of the present invention, one or more substances are included in one or more cavities of the screw, nail or post. In one aspect of this embodiment, one or more cavities includes a single type of substance. In still another and/or alternative embodiment of the present invention, the cavity includes a multiple types of substances. In yet another and/or alternative embodiment of the present invention, one or more cavities can be partially or fully filled with one or more substances. In still yet another and/or alternative embodiment of the present invention, the one or more substances are partially or fully coated on the surface of the screw, nail or post.

In yet another and/or alternative aspect of the present invention, the one or more access openings in the surface of the screw, nail or post allow insertion of one or more substances into one or more cavities of the screw, nail or post; allow one or more substances to exit the one or more cavities of the screw, nail or post; and/or to allow body fluids and/or bone growth into the one or more access openings and/or into the one or more cavities. In one embodiment of the present invention, a plurality of cavities includes at least one access opening. In another and/or alternative embodiment of the present invention, at least one access opening can be used by the manufacturer and/or physician to inserted one or more substances into one or more cavities. As can be appreciated, a physician can add a substance into the cavity just prior to, during, and/or after the insertion of the screw, nail, or post in the bone and/or cartilage. As can further be appreciated, a physician can add a substance into the cavity after the surgery has been completed and the patient is recovering from the surgery. In such a situation, the cavity can be periodically replenished with the same or different substance to facilitate in the recovery of the patient. In still another and/or alternative embodiment, the size of one or more of the access openings is selected to control or regulate the flow of substances into and/or out of the one or more access openings.

In still yet another and/or alternative aspect of the present invention, a cap and/or cover is applied over one or more access openings. The cap or cover is designed to at least partially seal one or more substances in the one or more cavities and/or access openings, and/or to at least partially control the release of one or more substances from the one or more cavities. In one embodiment of the invention, the cap or cover is be made of a biodegradable and/or non-biodegradable material. In one aspect of this embodiment, the cap and/or cover is at least partially made of a biodegradable material which at least partially dissolves after the screw, nail or post has been implanted thereby at least partially providing access to the access opening over time. In another and/or alternative embodiment of the invention, the cap and/or cover can be inserted prior to, during, and/or after the insertion of the screw, nail, or post in the bone and/or cartilage. In still another and/or alternative embodiment of the invention, the cap and/or cover can be designed to be at least partially removed prior to, during, and/or after the insertion of the screw, nail, or post in the bone and/or cartilage. In yet another and/or alternative embodiment of the invention, the cap and/or cover is at least partially made of a material that allows one of more substances and/or body fluids to penetrate the cap or cover. In still yet another and/or alternative embodiment of the present invention, the cap and/or cover material includes, but is not limited to, metals, wood, fabric, carbon and/or glass fibers, polymers; copolymers; human tissue; animal tissue; synthetic tissue; human cells; animal cells; synthetic cells; and/or bone-stimulation, bone-growth and/or bone activating matter. In a further and/or alternative embodiment of the present invention, the cap and/or cover can be applied to the screw, nail or post is a number of ways (e.g., dipping, spraying, ionizing, painting, adhesive, screwing, snapping, locking, tacking, soldering, melting, etc.).

In a further and/or alternative aspect of the invention, the screw, nail or post includes one or more outer surface regions that are coated with one or more substances. In one embodiment of the present invention, the one or more substances include, but are not limited to, a substance that a) promotes and/or inhibits bone and/or other tissue growth, b) inhibits rejection of the screw, nail or post, c) inhibits rejection of components connected to and/or located adjacent to the screw, nail or post, d) reduces infection, e) reduces inflammation, f) reduces pain, g) provides vitamins, minerals, and/or nutrients, h) provides genetic material, i) provides tissue, j) facilitates in the insertion, positioning, and/or removal of the screw, nail or post from bone and/or cartilage (e.g. lubricant, Teflon, graphite, etc.), k) secures the screw, nail or post in the bone and/or cartilage (e.g. bone cement or other adhesive, etc.), l) promotes healing of surrounding tissue, m) combats cancer and/or other diseases, n) combats and/or cures biological abnormalities (e.g. chemical imbalance, etc.), o) functions as a location and/or visual indicator, and/or the like. Typically, the one or more coated substances is selected to improve the success of retaining the screw, nail, or post into the bone and/or cartilage. In another and/or alternative embodiment of the present invention, the coating includes a single type of substance. In still another and/or alternative embodiment of the present invention, the coating includes a multiple types of substances. In another and/or alternative embodiment of the present invention, the surface of the screw, nail or post that includes the one or more substances is smooth, rough (e.g., ribs, canals, pits, teeth, ridges, grooves, holes, notches, slits, slots, channels, corrugations etc.), porous and/or non-porous. In yet another and/or alternative embodiment of the present invention, the coating is smooth and/or rough. In still yet another and/or alternative embodiment of the present invention, the coating includes a compound that at least partially controls the release of the one or more substances from the coating. The compound can be biodegradable or non-biodegradable. In still yet another and/or alternative embodiment of the present invention, the coating facilitates the insertion and/or securing of the screw into bone and/or cartilage. In one aspect of this embodiment, the coating is a biocompatible material. In another and/or alternative aspect of this embodiment, the coating includes polytetrafluoroethylene, or polymers and/or co-polymers that includes polytetrafluoroethylene, a natural and/or synthetic bone cement; polymer, co-polymer and/or urethane foam; autologous growth compound; powdered bone, bone and/or other tissue growth stimulating substances; polyglycolate polymers and/or analogues; lactides; polydioxamone; polyglycolate; lactide/glycolide copolymers; and/or other tissue growth inhibiting compounds; and/or other substances (e.g., antithrombogenic agents; steroids; thioprotese inhibitors; antimicrobials; antibiotics; tissue plasma activators; monoclonal antibodies; antifibrosis compounds; hormones; growth factors; anti-mitotic agents; immunosuppressive agents; sense or antisense oligonucleotides; nucleic acid analogues; inhibitors of transcription factor activity; antineoplastic compounds; chemotherapeutic compounds; radioactive agents; growth factors; antiplatlet compounds; antitabolite compounds; anti-inflammatory compounds; anticoagulent compounds; antimitotic compounds; antioxidants; antimetabolite compounds; anti-migratory agents; anti-matrix compounds; anti-vital compounds; anti-proliferatives; anti-fungal compounds; anti-protozoal compounds; human tissue; animal tissue; synthetic tissue; human cells; animal cells; synthetic cells; and/or bone-stimulation, bone-growth and/or bone activating matter; etc.). In a further embodiment of the present invention, the coated material can be applied to the screw, nail or post by adhesive bonding, welding, soldering, shrink wrapping, melting, spray coating, ionization, hot dipping, electroplating, immersion coating, brush coating, and/or the like. In another embodiment, the coating material enhances the strength and/or durability of the screw, nail or post and/or hardens or softens the surface of the screw, nail or post. In still and/or alternative embodiment of the present invention, the one or more coatings of one or more substances are partially or fully coated on the surface of the screw, nail or post.

In another and/or alternative aspect of this invention, the screw, nail or past includes at least one opening or mounting member used to connect and/or secure a) one or more devices to anchor and/or affix one or more components of the implant (e.g. rod, cage, stabilization system, screw, post, etc.), and/or b) one or more components of the screw, nail or post (e.g. connect head to lower portion of screw, nail or post; connect an electrical and/or electronic component to the screw, nail or post; connect a mechanical component to the screw, nail or post; etc.). the one or more opening can be an access opening as described above, or some other opening. The one or more mounting members can be, but are not limited to, a ridge, groove, slot, etc. The one or more openings or mounting members can be positioned on the head and/or lower portion of the screw, nail or post.

In yet another and/or alternative aspect of the invention, the screw, nail or post includes one or more mechanical and/or electrical devices that at least partially cause and/or control the release of one or more substances from the screw, nail or post. In one embodiment of the present invention, the mechanical and/or electrical device can be designed to cause and/or control the release of one or more substances based upon, but not limited to, a) a preprogrammed schedule, b) a function of time, c) a predetermined rate, d) and/or receipt of an external signal. In one aspect of this embodiment, the mechanical and/or electrical device is preprogrammed to allow and/or cause the release one or more substances from the screw, nail or post during one or more time periods. In one non-limiting design, the mechanical and/or electrical device includes a microchip that at least partially stores a program that allows and/or causes the release one or more substances from the screw, nail or post. In one particular design, the mechanical and/or electrical device includes one or more MEMS (micro-electro-mechanical systems). The MEMS include both the preprogramming and the mechanism to allow and/or cause the release one or more substances from the screw, nail or post. In another and/or alternative particular design, the microchip at least partially controls a separate mechanical and/or electrical device (e.g., valve, pump, motor, etc.) which in turn allows and/or causes the release one or more substances from the screw, nail or post. In still another and/or alternative particular design, the microchip can be preprogrammed and/or reprogrammed prior to, during and/or after the insertion of the screw, nail or post. As can be appreciated, the parameters for allowing and/or causing the release of one or more substances can be altered by reprogramming (e.g., new data, additional data, new source code, additional source code, etc.) during the healing process of a patient, thus are individualized for a patient. Consequently, the setting for the mechanical and/or electrical device can be changed, as medical treatment needs dictate.(e.g. greater or lesser amounts of substance discharge, different substance discharge ratios, more frequent substance discharge, etc.). In yet another and/or alternative particular design, the microchip can be activated prior to, during and/or after the insertion of the screw, nail or post. In another and/or alternative aspect of this embodiment, the external signal includes, but is not limited to, an electrical signal, magnetic signal, electromagnetic wave signal (e.g. light, radio wave, microwave, x-ray, infrared light, ultraviolet light, etc.), heat signal, vibration signal, chemical signal, mechanical signal, etc. In yet another and/or alternative embodiment of the present invention, a transmitter (e.g. wire, fiber optic cable, electromagnetic wave transmitter, etc.) is connected between the screw, nail or post and at or near the surface of the patient's body and/or some other location, which transmitter allows a signal to be transmitted from a remote location to the screw, nail or post. In one aspect of this embodiment, the signal can a) transmit a signal to the mechanical or electrical device in the screw, nail or post; and/or b) provide instructions and/or programming to the mechanical or electrical device in the screw, nail or post. In still yet a further and/or alternative embodiment of the present invention, the mechanical and/or electrical device can be activated prior to, during, or after the insertion of the screw, nail or post in the bone and/or cartilage. In another and/or alternative aspect of this embodiment, one or more contact points are located at or near the surface of the skin of a human or animal, which one or more contacts are connected between a contact surface of the contact points and the screw, nail or post, and/or one or more components connected to the screw, nail or post. In still another and/or alternative aspect of this embodiment, the screw, nail or post, and/or one or more components connected to the screw, nail or post, includes an electromagnetic wave transmitter and/or receiver which can send and/or receive signals in the form of electromagnetic waves. In still yet a further and/or alternative embodiment of the present invention, the mechanical and/or electrical device can be activated prior to, during, or after the insertion of the screw, nail or post in the bone and/or cartilage. In still a further and/or alternative embodiment of the invention, the mechanical and/or electrical device can at least partially control the location of substance discharge on the screw, nail or post; and/or control the amount and/or frequency of substance discharge on various regions of the screw, nail or post. In one aspect of this embodiment, the mechanical and/or electrical device can open and/or close one or more access openings, and/or cause one or more substances to flow into and/or out of one or more cavities. In still another and/or alternative embodiment, the amount of substance discharge from the screw, nail or post is at least about 0.001 milliliters per discharge, and generally about 0.002–20 milliliters per discharge; however, other discharge amounts can occur.

In still yet another and/or alternative embodiment of the present invention, the screw, nail or post is designed such that one or more cavities can be filled and/or refilled with one or more substances after being inserted in bone and/or cartilage. The filling and/or refilling of one or more cavities in the screw, nail or post facilitates in an ongoing or a sequence of therapies that can be applied at and/or contiguous to the site of insertion of the screw, nail or post. In one embodiment of the present invention, the screw, nail or post includes one or more access openings designed to receive an end of a syringe or other device that is adapted to insert a substance in the access opening. In another and/or alternative embodiment of the present invention, a tube is connected between the screw, nail or post and the surface of the patient's body, which tube includes an opening designed to receive an end of a syringe or other device adapted to insert a substance in the tube opening which in turn conveys the substance to an access opening in the screw, nail or post.

In still a further and/or alternative embodiment of the present invention, the screw, nail or post includes one or more mechanisms to promote bone healing about the screw, nail or post and/or adjacent to the screw, nail or post. In one embodiment of the present invention, the screw, nail or post applies an electrical charge on or about the screw, nail or post. Electrical stimulation has been found, in certain situations, to promote the healing of bone and/or other tissue. The use of such electrical stimulation can promote the healing of bone and/or cartilage about the screw, nail or post. In another and/or alternative embodiment of the present invention, the screw, nail or post includes one or more mechanical and/or electrical devices that at least partially control the duration, timing and/or degree of electrical stimulation from the screw, nail or post. In one aspect of this embodiment, the mechanical and/or electrical device can be designed to control the duration, timing and/or degree of electrical stimulation based upon a preprogrammed sequence, as a function of time, and/or upon receipt of an external signal. In one non-limiting design, the mechanical and/or electrical device is preprogrammed to control the duration, timing and/or degree of electrical stimulation from the screw, nail or post. In one particular non-limiting design, the mechanical and/or electrical device includes a microchip that at least partially stores a program that allows and/or causes the occurrence of an electrical stimulation from the screw, nail or post. In another and/or alternative non-limiting particular design, the mechanical and/or electrical device includes one or more MEMS (micro-electro-mechanical systems). The MEMS includes both the preprogramming and the mechanism that allows and/or causes the occurrence of an electrical stimulation from the screw, nail or post. In still another and/or alternative non-limiting particular design, the microchip at least partially controls a separate mechanical and/or electrical device (e.g. battery, electric generator, etc.) which in turn allows and/or causes an electrical simulation to occur. In still another and/or alternative non-limiting particular design, the microchip can be preprogrammed and/or reprogrammed prior to, during and/or after the insertion of the screw, nail or post. As can be appreciated, the parameters for electrical stimulation can be altered by reprogramming (e.g., new data, additional data, new source code, additional source code, etc.) during the healing process of a patient, thus are individualized for a patient. Consequently, one or more settings for the mechanical and/or electrical device can be changed, as medical treatment needs dictate (e.g. greater or lesser stimulation, a more frequent electrical discharge, adjustments of time and/or power of electrical discharge, etc.). In yet another and/or alternative non-limiting particular design, the microchip can be activated prior to, during and/or after the insertion of the screw, nail or post. In another and/or alternative aspect of this embodiment, the external signal includes, but is not limited to, an electrical signal, magnetic signal, electromagnetic wave signal (e.g. light, radio wave, microwave, x-ray, infrared light, etc.), heat signal, vibration signal, chemical signal, mechanical signal, etc. In another and/or alternative embodiment of the invention, mechanical and/or electrical component can be charged prior to, during and/or after insertion of the screw, nail or post. In still another and/or alternative embodiment of the invention, mechanical and/or electrical component can be recharged after insertion of the screw, nail or post. In yet another and/or alternative embodiment of the present invention, a transmitter (e.g. wire, fiber optic cable, electromagnetic wave transmitter, etc.) is connected between the screw, nail or post and at or near the surface of the patient's body and/or some other location, which transmitter allows an electrical current and/or signal to be transmitted from a remote location to the screw, nail or post. In one aspect of this embodiment, the electrical current and/or signal can a) transmit a signal to the mechanical or electrical device in the screw, nail or post; b) recharge the mechanical and/or electrical device in the screw, nail or post; c) provide instructions and/or programming to the mechanical or electrical device in the screw, nail or post; d) generates and/or causes electrical simulation to be generated from the screw, nail or post. In another and/or alternative aspect of this embodiment, one or more contact points are located at or near the surface of the skin of a human or animal, which one or more contacts are connected between a contact surface of the contact points and the screw, nail or post, and/or one or more components connected to the screw, nail or post. In still another and/or alternative aspect of this embodiment, the screw, nail or post, and/or one or more components connected to the screw, nail or post, include an electromagnetic wave transmitter and/or receiver which can send and/or receive signals in the form of electromagnetic waves. In still yet a further and/or alternative embodiment of the present invention, the mechanical and/or electrical device can be activated prior to, during, or after the insertion of the screw, nail or post in the bone and/or cartilage. In a further and/or alternative embodiment of the invention, the electrical stimulation is at least partially generated by a battery, chemical reaction, generator, magnetic field, electric current, and/or the like. In still a further and/or alternative embodiment of the invention, the mechanical and/or electrical device can at least partially control the location of discharge on the screw, nail or post; and/or control the degree and/or frequency of discharge on various regions of the screw, nail or post. In one aspect of this embodiment, the mechanical and/or electrical device can relocate the location of electrical discharge on the screw, nail or post to promote healing in specified regions about the screw, nail or post. In another and/or alternative aspect of this embodiment, the mechanical and/or electrical device can regulate the amount of electrical discharge from one or more regions on the screw, nail or post to promote healing in specified regions about the screw, nail or post. In still another and/or alternative embodiment, the amount of voltage discharge from the screw, nail or post is at least about 1 microvolt per discharge, and generally about 5 microvolts to about 12 volts per discharge; however, other voltage amounts can be used. In yet another and/or alternative embodiment, the amount of current discharge from the screw, nail or post is at least about 1 microampere per discharge, and generally about 2 microamperes to about 0.1 amperes per discharge; however, other amperages can be used.

In yet a further and/or alternative aspect of the present invention, the screw, nail or post can be designed to be left in place for an indeterminate time after completion of surgery and post-surgical healing and/or can be removed at some time after the completion of surgery, or be replaced during ongoing therapy and/or treatment.

In still yet a further and/or alternative aspect of the present invention, the screw, nail or post is designed to be connected to a mechanical and/or electrical device which mechanical and/or electrical device at least partially regulates and/or controls the discharge of a substance and/or electrical current from at least a portion of the screw, nail or post. In one embodiment of the present invention, the mechanical and/or electrical device is connected to the screw, nail or post prior to, during or after insertion of the screw, nail or post into the bone and/or cartilage. In another and/or alternative embodiment of the present invention, the mechanical and/or electrical device is detachable from the screw, nail or post prior to, during or after insertion of the screw, nail or post into the bone and/or cartilage. In one aspect of this embodiment, the mechanical and/or electrical device can be replaced when it breaks, malfunctions, and/or has completed its useful life, without having to fully or partially remove the screw, nail or post from the bone and/or cartilage. In still another and/or alternative embodiment of the present invention, the screw, nail or post includes one or more openings, connection locations, and/or contact points for the connection of one or more mechanical and/or electrical devices to the screw, nail or post. The one or more openings, connection locations, and/or contact points can function to secure the mechanical and/or electrical device to the screw, nail or post, and/or to integrate the mechanical and/or electrical device with one or more cavities and/or other mechanical and/or electrical devices in the screw, nail or post.

In another and/or alternative aspect of the present invention, the screw, nail or post is designed such that a mechanical and/or electrical device at least partially regulates and/or controls the discharge of a substance and/or electrical current from at least a portion of the screw, nail or post is at least partially formed and/or positioned in the screw, nail or post. In one embodiment of the present invention, the majority of the mechanical and/or electrical device is embedded in the screw, nail or post prior to, during or after insertion of the screw, nail or post into the bone and/or cartilage. In another and/or alternative embodiment of the present invention, at least a portion of the mechanical and/or electrical device is connected to a portion of the mechanical and/or electrical device that is already at least partially formed and/or positioned in the screw, nail or post.

In still another and/or alternative aspect of the present invention, the screw, nail or post is formed of a substantially inert or biologically compatible material for use in humans. In one embodiment of the present invention, the screw, nail or post is designed to be used with a prosthetic implant that is designed to be placed in the intervertebral disc space that was formerly occupied by at least a portion of an intervertebral disc. In still another and/or alternative embodiment of the present invention, the prosthetic implant is designed to be readily inserted by established surgical procedures, with minimal chances of surgical difficulty. In yet another and/or alternative embodiment of the present invention, the screw, nail or post includes, but is not limited to, bone, stainless steel, titanium, chromemolybdenum, cobalt chromium alloy, chrome or chrome alloys, cobalt or cobalt alloys, polycarbonate, polypropylene, polyethylene, polymethylmethacrylate, polysolfone types filled with glass and/or carbon fibers, and various types of carbon and fiber reinforced polymers. In one aspect of this embodiment, the material is wear resistant.

In accordance with yet another and/or alternative aspect of the present invention, the screw, nail or post includes one or more openings in the head and/or lower portion to facilitate in the positioning of the screw, nail or post relative to the bone or cartilage and/or to secure the screw, nail or post in the bone and/or cartilage. In one embodiment of the present invention, one or more of the openings in the screw, nail or post is adapted to receive an instrument for guiding, inserting, and/or removing the screw, nail or post in the bone and/or cartilage.

In accordance with still yet another and/or alternative aspect of the present invention, the screw, nail or post is at least partially connected to bone and/or cartilage after an opening in the bone and/or cartilage has been formed. Typically, the hole is formed by a drill or similar device. The size of the opening is typically selected to be smaller than the cross-sectional area of the screw, nail, or post; however, this is not required. The opening is typically inserted in the bone and/or cartilage to reduce damage to the bone and/or cartilage when the screw, nail or post is subsequently inserted in the bone and/or cartilage, and/or to provide a guide opening for insertion of the screw, nail or post.

It is an object of the present invention to provide an improved screw, nail or post for insertion into bone and/or cartilage.

It is another and/or alternative object of the present invention to provide a screw, nail or post that can be easily and efficiently positioned into bone and/or cartilage and which reduces the failure rate of prosthetic implants.

It is still another and/or alternative object of the present invention to provide a screw, nail or post for securing a rod or elongate member from rotational and translational movement within a bone and/or cartilage.

It is yet another and/or alternative object of the present invention to provide a screw, nail or post which is relatively small and which can be readily manipulated.

It is still yet another and/or alternative object of the present invention to provide a screw, nail or post that can be manufactured with present conventional technology.

It is a further and/or alternative object of the present invention to provide a screw, nail or post that is designed to simplify the insertion and fixing of a prosthetic implant.

It is still a further and/or alternative object of the present invention to provide a screw, nail or post that is relatively easy to manufacture and cost effective to manufacture.

It is yet a further and/or alternative object of the present invention to provide a screw, nail or post that includes one or more cavities which is used to alter the weight distribution of the screw, nail or post; alter the structural integrity of the screw, nail or post; to at least partially contain a substance such as, but not limited to, a material that a) promotes and/or inhibits bone and/or other tissue growth, b) inhibits rejection of the screw, nail or post, c) inhibits rejection of components connected to and/or located adjacent to the screw, nail or post, d) reduces infection, e) reduces inflammation, f) reduces pain, g) provides vitamins, minerals, and/or nutrients, h) provides genetic material, i) provides tissue, j) facilitates in the insertion, positioning, and/or removal of the screw, nail or post from bone and/or cartilage (e.g. lubricant, Teflon, graphite, etc.), k) secures the screw, nail or post in the bone and/or cartilage (e.g. bone cement or other adhesive, etc.), l) promotes healing of surrounding tissue, m) combats cancer and/or other diseases, n) combats and/or cures biological abnormalities (e.g. chemical imbalance, etc.), o) functions as a location and/or visual indicator, and/or the like, and/or to at least partially contain one or more electrical and/or mechanical components.

It is still yet a further and/or alternative object of the present invention to provide a screw, nail or post that includes at least one cavity that has at least one access opening to the surface of the screw, nail or post.

It is another and/or alternative object of the present invention to provide a screw, nail or post that allows for insertion of one or more substances into one or more cavities of the screw, nail or post; that allows one or more substances to exit the one or more cavities of the screw, nail or post; and/or that allows body fluids and/or bone growth into the one or more access openings and/or into the one or more cavities.

It is still another and/or alternative object of the present invention to provide a screw, nail or post that allows a physician to insert one or more substances into one or more cavities prior to, during, and/or after the insertion of the screw, nail, or post in the bone and/or cartilage.

It is yet another and/or alternative object of the present invention to provide a screw, nail or post that includes a cap and/or cover that is applied over one or more access openings which is designed to at least partially seal one or more substances in the one or more cavities, and/or to at least partially control the release of one or more substances from the one or more cavities.

It is still yet another and/or alternative object of the present invention to provide a screw, nail or post that includes one or more outer surface regions that are coated with one or more substances.

It is a further and/or alternative object of the present invention to provide a screw, nail or post that includes one or more mechanical and/or electrical devices that at least partially control the release of one or more substances from the screw, nail or post.

It is still a further and/or alternative object of the present invention to provide a screw, nail or post that is designed such that one or more cavities can be filled and/or refilled with one or more substances after being inserted in bone and/or cartilage.

It is yet a further and/or alternative object of the present invention to provide a screw, nail or post that applies an electrical charge on or about the screw, nail or post.

These and other objects of the invention will become apparent to those skilled in the art upon reading and understanding the following detailed description of preferred embodiments taken together with the drawings.

BRIEF DESCRIPTION OF THE DRAWINGS

The invention may take physical form in certain parts and arrangement of parts, preferred embodiments of which will be described in detail and illustrated in the accompanying drawings which form a part hereof and wherein.

DESCRIPTION OF THE PREFERRED EMBODIMENTS

Figure 1:
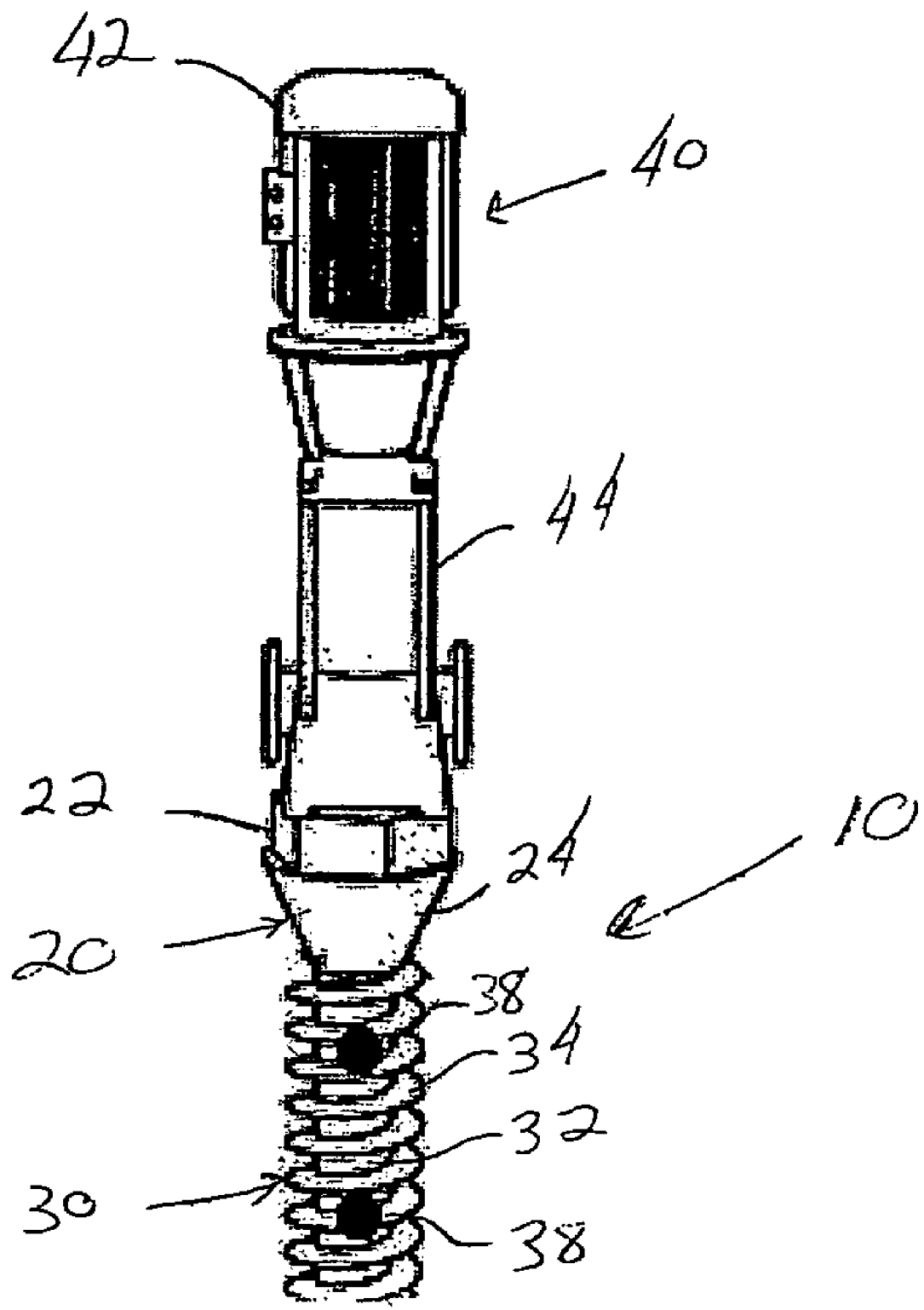
FIG. 1 is a partial perspective view of the front side pedicle screw of the present invention which includes a pump mechanism connected to top of the pedicle screw.

Referring to the drawings, wherein the showings are for the purpose of illustrating the preferred embodiment of the invention only and not for the purpose of limiting same, FIG. 1 illustrates a novel pedicle screw 10 for insertion into bone and/or cartilage. The pedicle screw will be describe with particular reference for use with surgical procedure involving the vertebra; however, it will be appreciated that the pedicle screw can be used in other regions of a body (e.g., leg, arm, hand, foot, pelvis, rib cage, scull, etc.) to promote healing in such regions.

Orthopedic surgeons, as well as neurosurgeons, have long recognized the need for the use of pedicle screws in the treatment of spinal pathologies, deformities and traumas. The pedicle screws are typically placed in the vertebral pedicle since this area has been long recognized as the "force nucleus" of the spinal vertebra, i.e. the area of the spine where a force applied to the bone by pedicle screw would have the highest mechanical advantage in repositioning the bone. The pedicle screw can be used by a surgeon in other procedures, such as anchoring tissue or in bone plating systems.

Figure 2:
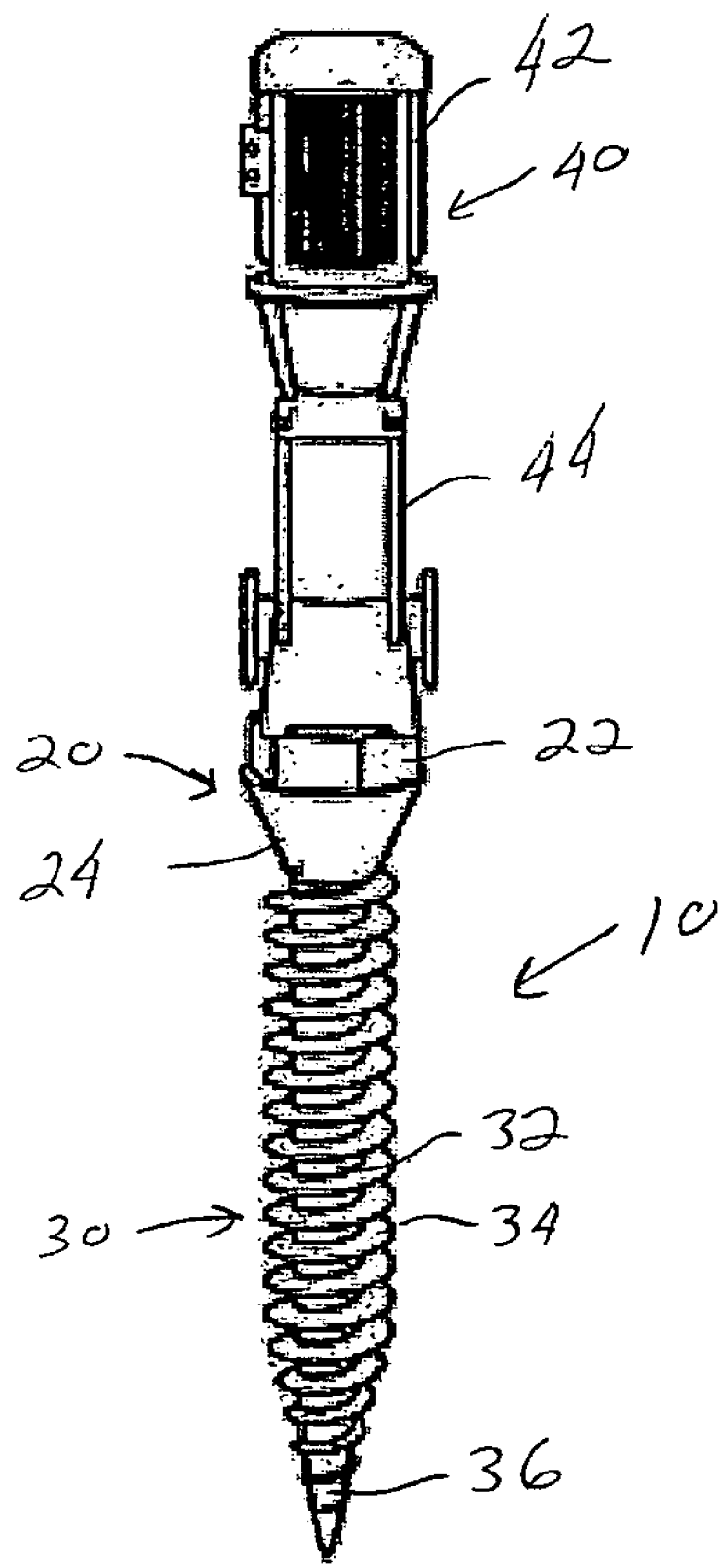
FIG. 2 is a perspective view of the back side of the pedicle screw of FIG. 1.

Referring again to FIG. 1, the pedicle screw 10 is fabricated of a well known biocompatible material such as stainless steel or titanium, and has a head 20 and a lower portion 30. The particular material or materials selected will generally depend on the location of the pedicle screw and the various objectives to be accomplished by the pedicle screw. Head 20 has a hexagonal cross-sectional shaped top portion to facilitate in the insertion of the pedicle screw into the bone and/or cartilage. As can be appreciated, other shapes of the top portion can be used (e.g., octagonal, triangular, square, etc.). As can also be appreciated, the top portion 22 can include one or more indentations, slots, ridges, openings, etc. to facilitate in the insertion of the pedicle screw into the bone and/or cartilage. Positioned below the hexagonal top portion is a conical shaped portion 24 that terminates at the lower portion 30 of the pedicle screw. The lower portion of the pedicle screw includes an outer surface 32 that includes thread 34. The cross-sectional shape of the lower portion is substantially circular and has a substantially constant cross-sectional shape and cross-sectional area throughout the majority of the longitudinal length of the lower portion. The end 36 of the lower portion as illustrated in FIG. 2 tapers to a point; however, the end 36 can have a substantially flat configuration and/or have a non-tapering configuration. As can be appreciated, many other shapes and/or configurations of the head and/or lower portion can be used for the pedicle screw in the present invention.

In utilizing the pedicle screw, the pedicle screw is typically inserted into the bone and/or cartilage that includes a tapped or pre-drilled hole formed therein as a guide for the placement of the screw. The bone has a relatively hard compact shell, which encases a loose spongy cancellous bone material. The tap or pre-drilled hole facilitates in the insertion of the pedicle screw into the bone and/or minimizes damage to the bone during the insertion of the pedicle screw. Typically the tap or pre-drilled hole has a diameter that is less than the threads 34 on the lower portion 30 of the pedicle screw. For example, the tap or pre-drilled hole may have a diameter of about 8 mm, and the threads on the lower portion of the pedicle screw have a diameter of about 8.5 mm. The tap hole or pre-drilled hole forms a precise, preset path of insertion for the pedicle screw. Since the threads have a larger diameter that the opening in the bone and/or cartilage, the thread 34 bites into the bone and/or cartilage thereby accurately positioning the pedicle screw in the bone and/or cartilage and securing the pedicle screw in the bone and/or cartilage. Typically the pedicle screw is adapted for use in securing a plate, rod and/or the like, not shown, from translational or rotational motion.

Referring again to FIG. 1, a mechanical mechanism 40 is connected to top portion 22. The mechanical mechanism can be connected to the top portion is a variety of way such as, but not limited to, screw, bolt, solder, weld, latch, snap, clip, etc. The connection can be designed to allow the mechanical mechanism to be at least partially connected to the top portion prior to, during, and/or after the pedicle screw has been inserted into the bone and/or cartilage. Alternatively and/or additionally, the connection can be designed to allow the mechanical mechanism to be at least partially removably connected to the top portion of the pedicle screw. Still alternatively and/or additionally, the connection can be designed to be at least partially irremovably connect one or more components of the mechanical mechanism to the top portion of the pedicle screw.

As illustrated in FIGS. 1 and 2, mechanical mechanism 40 includes a pump 42 and a cylinder 44 that is connected between pump 42 and top portion 22 of head 20. The pump can have any number of different configurations and/or can operate in any number of different ways. The pump is specifically designed to cause a substance contained in the cylinder to flow out of the cylinder. In one non-limiting configuration, the pump includes a piston that at least partially travels into the cylinder to cause one or more substances in the cylinder to flow out of the cylinder.

The substance in the cylinder can include a variety of materials that promote bone and/or other tissue growth, inhibit rejection of the prosthetic implant, reduce infection, reduce inflammation, reduce pain, promote healing of surrounding tissue, function as a location and/or visual indicator, and/or the like. Such substances include, but are not limited to, antithrombogenic agents; steroids; thioprotese inhibitors; antimicrobials; antibiotics; tissue plasma activators; monoclonal antibodies; antifibrosis compounds; hormones; growth factors; anti-mitotic agents; immunosuppressive agents; sense or antisense oligonucleotides; nucleic acid analogues; inhibitors of transcription factor activity; anti-neoplastic compounds; chemotherapeutic compounds; radioactive agents; growth factors; antiplatlet compounds; antitabolite compounds; anti-inflammatory compounds; anticoagulent compounds; antimitotic compounds; antioxidants; antimetabolite compounds; anti-migratory agents; anti-matrix compounds; anti-vital compounds; anti-proliferatives; anti-fungal compounds; anti-protozoal compounds; human tissue; animal tissue; synthetic tissue; human cells, animal cells; synthetic cells; and/or bone-stimulation, bone-growth and/or bone activating matter.

Once the pedicle screw is connected to the bone and/or cartilage, the mechanical mechanism can be activated so that the pump causes one or more substances in the cylinder to flow out of the cylinder. The mechanical mechanism can alternatively be activated prior to complete insertion of the pedicle screw into the bone and/or cartilage. The activation of the mechanical mechanism can be manual and/or by a preprogrammed activation mechanism. The rate at which the pump causes one or more substances in the cylinder to flow out of the cylinder can be constant or manually and/or electronically regulated to vary over time.

Referring again to FIG. 1, the lower portion 30 of pedicle screw 10 includes two openings 38. As can be appreciated, more or less openings can be located in the lower portion. Furthermore, it can be appreciated that one or more openings can be located in the top portion of the pedicle screw. The openings are designed to allow at least a portion of the one or more substances in the cylinder 44 to flow out of the openings 38 and to the surrounding bone and/or cartilage. The top portion of the pedicle screw includes one or more openings, not shown, which allows the one or more substances from the cylinder 44 to flow into the one or more openings in the top portion and into one of more interior channels in the top portion, not shown. These one or more channels in the top portion allow the one or more substances to flow through the top portion and into one or more channels in the lower portion, not shown, and out through openings 38. The two or more openings can be positioned on the same side of the pedicle screw as illustrated in FIG. 1, or positioned in the lower portion in other manners.

Figure 3:
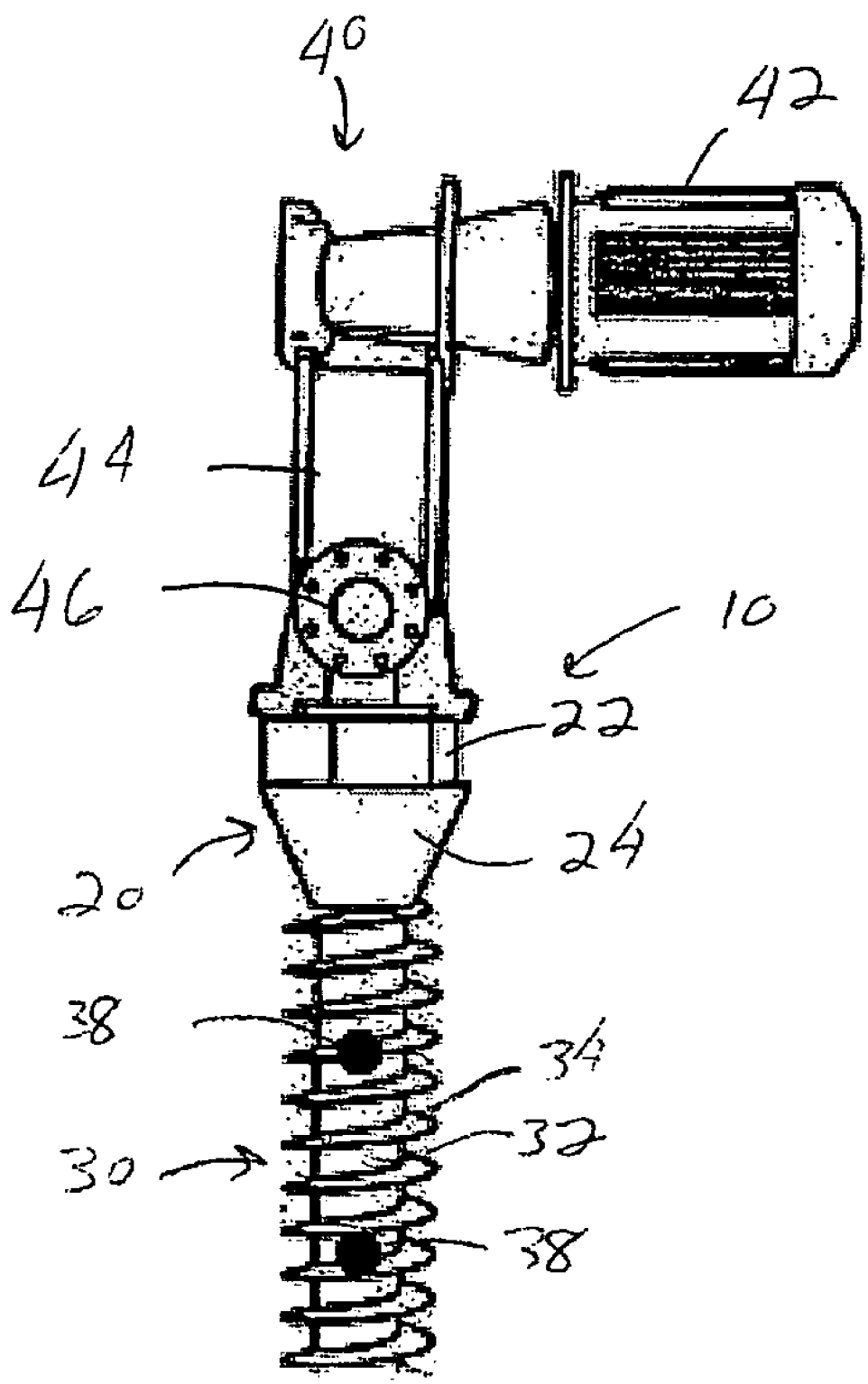
FIG. 3 is another partial perspective view of the front side pedicle screw of the present invention which includes a pump mechanism connected to top of the pedicle screw wherein the pump is oriented in a different position on the pedicle screw.
Figure 4:
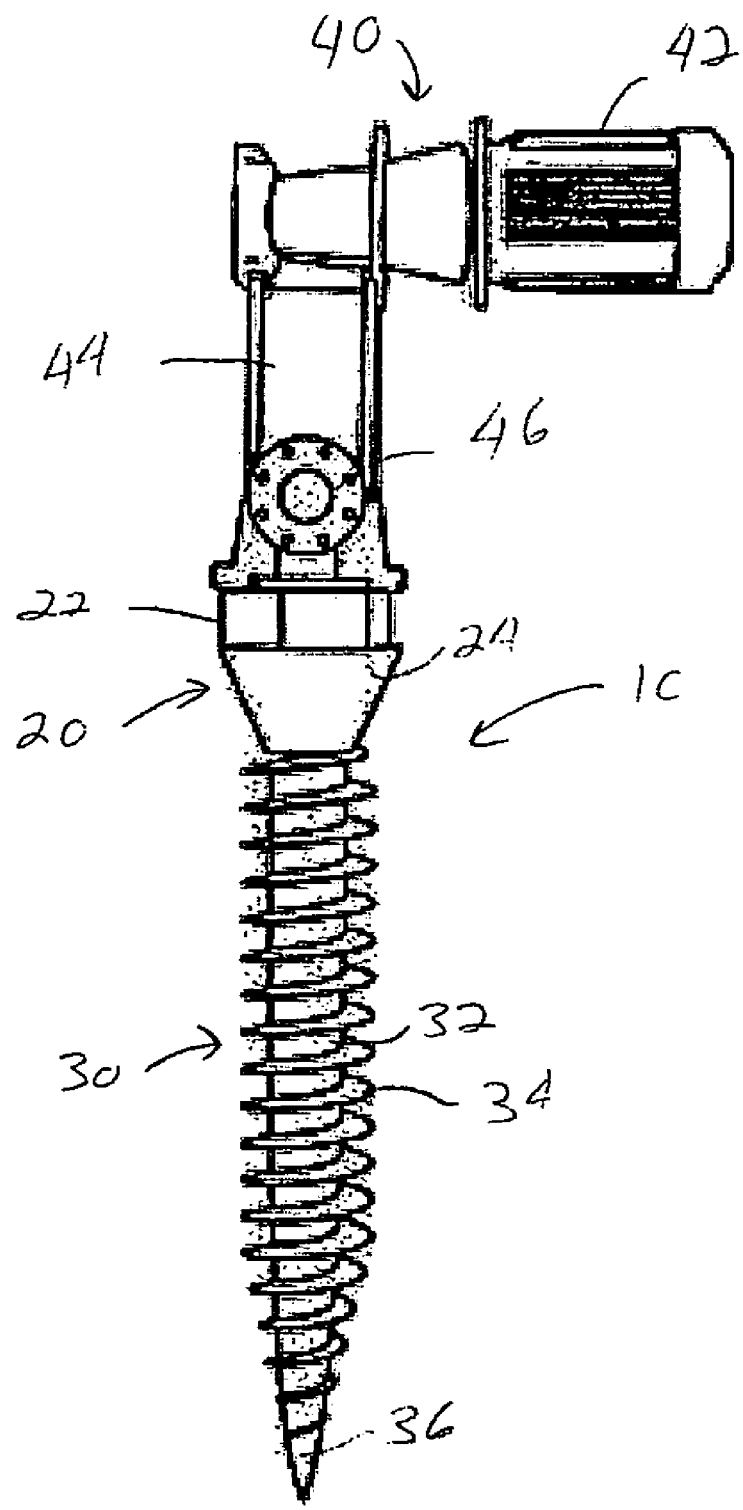
FIG. 4 is a perspective view of the back side of the pedicle screw of FIG. 3.

Referring now to FIGS. 3 and 4, another embodiment of the invention is illustrated. Pump 42 is shown to be attached to cylinder 44 so that the pump does not extend longitudinally above the cylinder. In this configuration, the pump does not extend as far outward from the pedicle screw. Such a pump orientation can facilitate the use of this embodiment in regions of the spine wherein the orientation of the pump as illustrated in FIGS. 1 and 2 may interfere with the surrounding tissue. As can be appreciated, pump 42 can be orientated in a variety of other manners to facilitate the use of the pump and successful use of the pedicle screw. FIGS. 3 and 4 also illustrates a flange 46 positioned on cylinder 44. The flange 46 allows one or more substances to be added to and/or removed from the cylinder prior to, during and/or after the pedicle screw is inserted into the bone and/or cartilage. The flange 46 can also be used to refill the cylinder.

Figure 5:
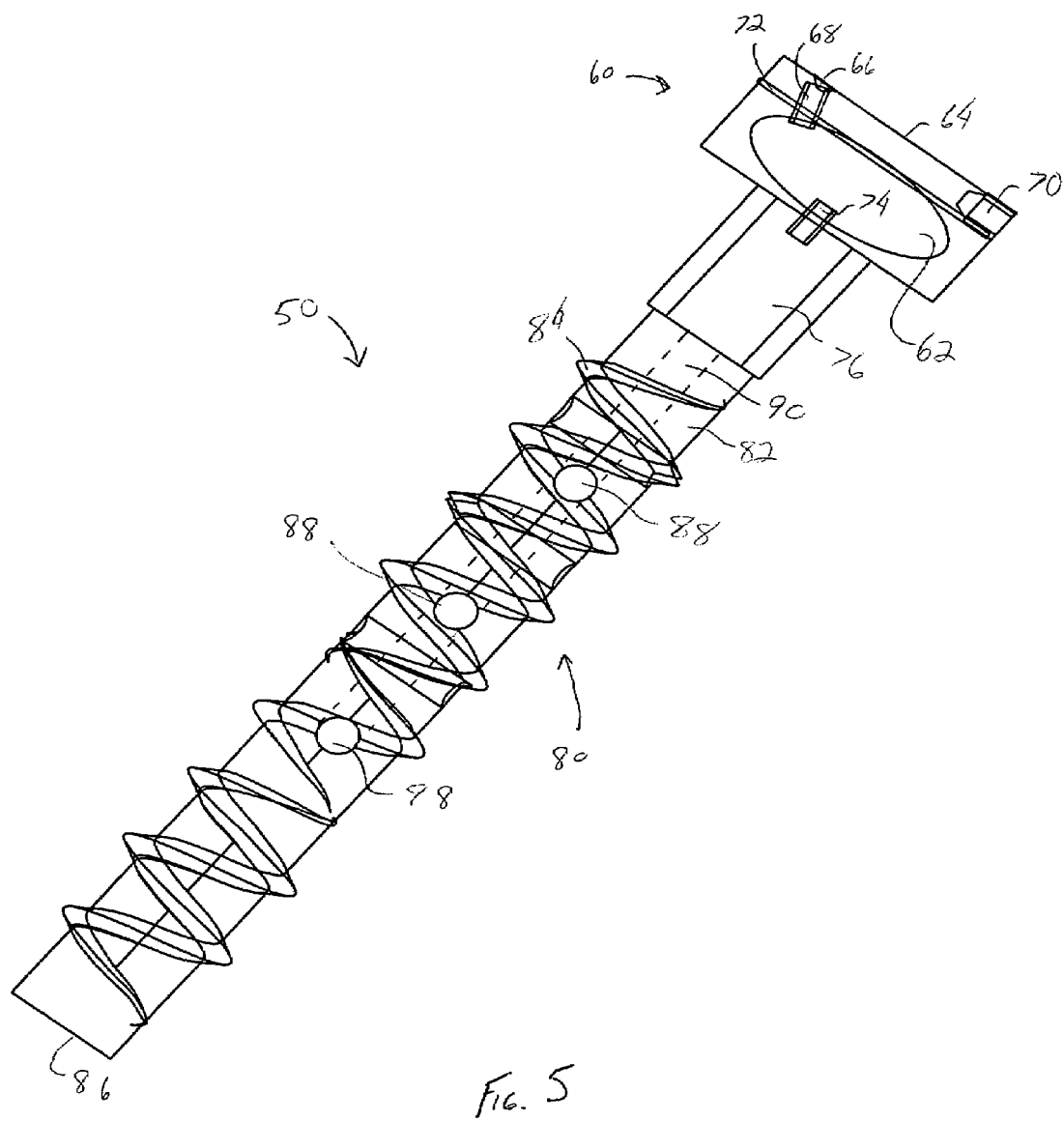
FIG. 5 is still another perspective view of the front side pedicle screw of the present invention which includes a pump mechanism positioned in the top of the pedicle screw.

Referring now to FIG. 5, still another embodiment of the invention is illustrated. Pedicle screw 50 includes a head 60 and a lower portion 80. The cross-section of head 60 illustrates that the head includes one or more reservoirs 62 for containing one or more substances described above. The reservoir is illustrated as having an ovoid shape; however, other shapes can be used. The top 64 of head 60 includes one or more port openings 66. Port opening 66 allows one or more substances to be inserted and/or removed from reservoir 62. One or more port passages 68 allows fluid passage between port opening 66 and reservoir 62. The port opening may have a sealing member to inhibit or prevent one or more substances in the reservoir from freely flowing out of the reservoir and out through port opening 66. One or more motors 70 are positioned in head 60. Motor 70 can be any type of motor that is small enough to be substantially fully positioned in the head. One non-limiting motor is a MEMS device. The head also includes one or more pressure plates 72 designed to be moved by motor 70 to thereby cause the one or more substances in reservoir 62 to flow out of the reservoir. One or more discharge ports 74 allow one or more substances to flow from the reservoir and into a base chamber 76 of head 60.

The lower portion 80 of the pedicle screw includes an outer surface 82 that includes thread 84. The cross-sectional shape of the lower portion is substantially circular and has a substantially constant cross-sectional shape and cross-sectional area throughout the majority of the longitudinal length of the lower portion. The end 86 of the lower portion is substantially flat. As can be appreciated, many other shapes and/or configurations of the head and/or lower portion can be used for the pedicle screw. The lower portion also includes three openings 88. As can be appreciated, more or less openings can be located in the lower portion. Furthermore, it can be appreciated that one or more openings can be located in the top portion of the pedicle screw. The openings are designed to allow at least a portion of the one or more substances to flow out of the openings 88 and to the surrounding bone and/or cartilage. The lower portion also includes one or more channels 90 to allow the one or more substances to flow from base chamber 76 of head 60 and out through openings 88. The two or more openings can be positioned on the same side of the pedicle screw as illustrated in FIG. 5, or be positioned on the lower portion in other manners.

As stated above, once the pedicle screw is connected to the bone and/or cartilage, the mechanical mechanism can be activated so that the pump causes one or more substances to flow out of openings 88. The mechanical mechanism can alternatively be activated prior to complete insertion of the pedicle screw into the bone and/or cartilage. The activation of the mechanical mechanism can be manual and/or by a preprogrammed activation mechanism. The rate at which the pump causes one or more substances in the cylinder to flow out of the cylinder can be constant or be manually and/or electronically regulated to vary over time.

Figure 6:
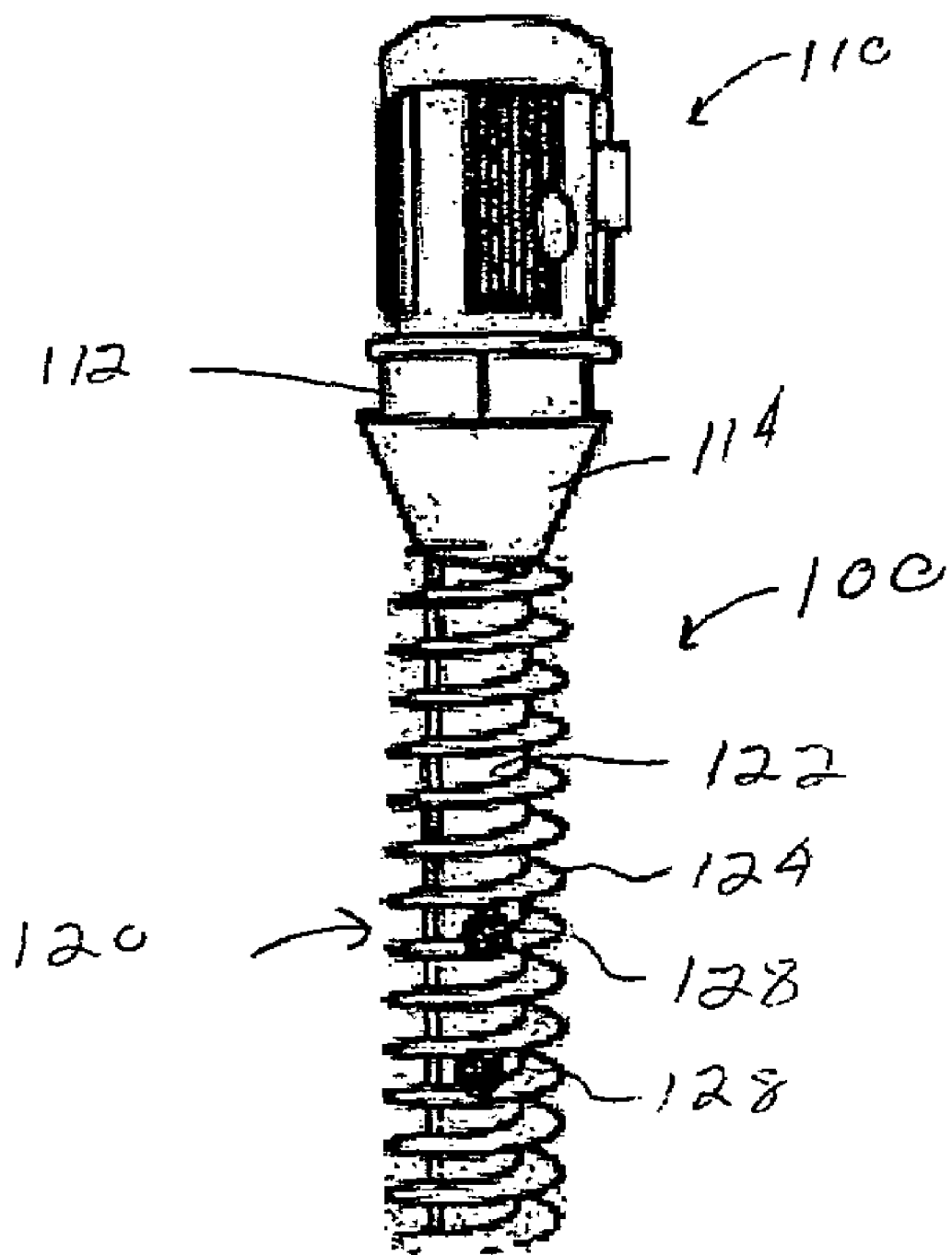
FIG. 6 is a partial perspective view of the front side pedicle screw of the present invention which includes a electrical mechanism connected to top of the pedicle screw.
Figure 7:
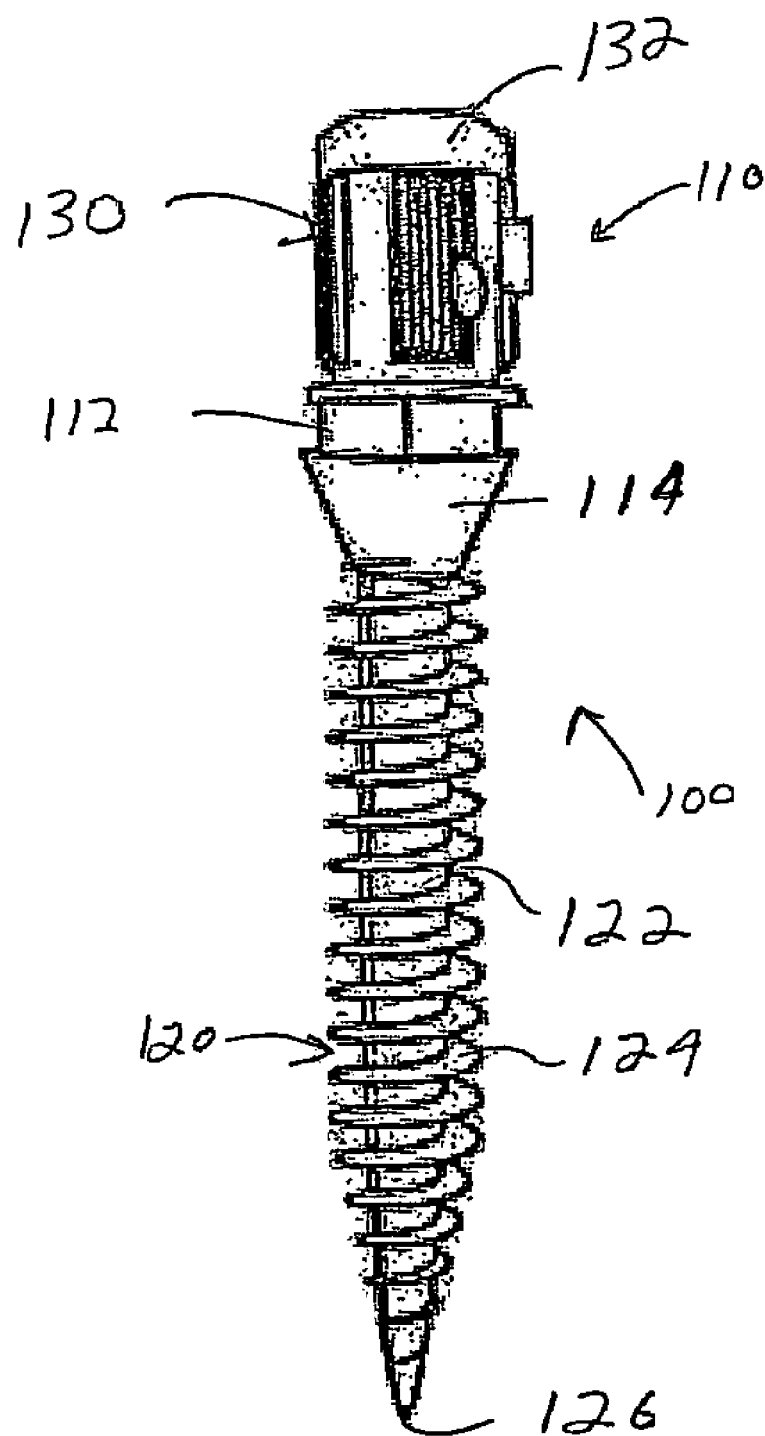
FIG. 7 is a perspective view of the back side of the pedicle screw of FIG. 6.

Referring now to FIGS. 6 and 7, another embodiment of the invention is disclosed. Pedicle screw 100 has a head 110 and a lower portion 120. Head 110 has a hexagonal cross-sectional shaped top portion 112 to facilitate in the insertion of the pedicle screw into the bone and/or cartilage. As can be appreciated, other shapes of the top portion can be used. As can also be appreciated, the top portion 112 can include one or more indentations, slots, ridges, openings, etc. to facilitate in the insertion of the pedicle screw into the bone and/or cartilage. Positioned below the hexagonal top portion is a conical shaped portion 114 that terminated at the lower portion 120 of the pedicle screw. The lower portion of the pedicle screw includes an outer surface 122 that includes thread 124. The cross-sectional shape of the lower portion is substantially circular and has a substantially constant cross-sectional shape and cross-sectional area throughout the majority of the longitudinal length of the lower portion. The end 126 of the lower portion as illustrated in FIG. 7 tapers to a point; however, the end 126 can have a substantially flat configuration and/or have a non-tapering configuration. As can be appreciated, many other shapes and/or configurations of the head and/or lower portion can be used for the pedicle screw in the present invention.

Referring again to FIG. 6, an electrical mechanism 130 is connected to top portion 112. The electrical mechanism can be connected to the top portion is a variety of way such as, but not limited to, screw, bolt, solder, weld, latch, snap, clip, etc. The connection can be designed to allow the electrical mechanism to be at least partially connected to the top portion prior to, during, and/or after the pedicle screw has been inserted into the bone and/or cartilage. Alternatively and/or additionally, the connection can be designed to allow the electrical mechanism to be at least partially removably connected to the top portion of the pedicle screw. Still alternatively and/or additionally, the connection can be designed to be at least partially irremovably connect one or more components of the electrical mechanism to the top portion of the pedicle screw.

As illustrated in FIGS. 6 and 7, the electrical mechanism includes a battery or electric generator 132 that is connected to top portion 112 of head 110. The battery or electric generator can have any number of different configurations and/or can operate in any number of different ways. The battery or electric generator is specifically designed to supply an electric current to one or more surfaces of the pedicle screw. In one non-limiting configuration, the electrical mechanism includes a battery to supply electric current to one or more regions on the pedicle screw.

Once the pedicle screw is connected to the bone and/or cartilage, the electrical mechanism can be activated so that the battery or electric generator begins supplying electric current to one or more regions on the pedicle screw. The electrical mechanism can alternatively be activated prior to complete insertion of the pedicle screw into the bone and/or cartilage. The activation of the electrical mechanism can be manual and/or by a preprogrammed activation mechanism.

The rate at which the electrical mechanism discharges electric current can be constant or manually and/or electronically regulated to vary over time.

Referring again to FIG. 6, the lower portion 120 of pedicle screw 100 includes two electrodes 128. As can be appreciated, more or less electrodes can be located in the lower portion. Furthermore, it can be appreciated that one or more electrodes can be located in the top portion of the pedicle screw. The electrodes are designed to conduct electrical current about the surrounding bone and/or cartilage. The top portion of the pedicle screw includes one or more regions, not shown, which allow current to be conducted between the battery or electric generator and the two or more electrodes in the lower portion. For example, the one or more regions can be a passageway for containing and electrically conducting material such as, but not limited to, a wire. The two or more electrodes can be positioned on the same side of the pedicle screw as illustrated in FIG. 6, or be positioned in the lower portion in other manners.

Figure 8:
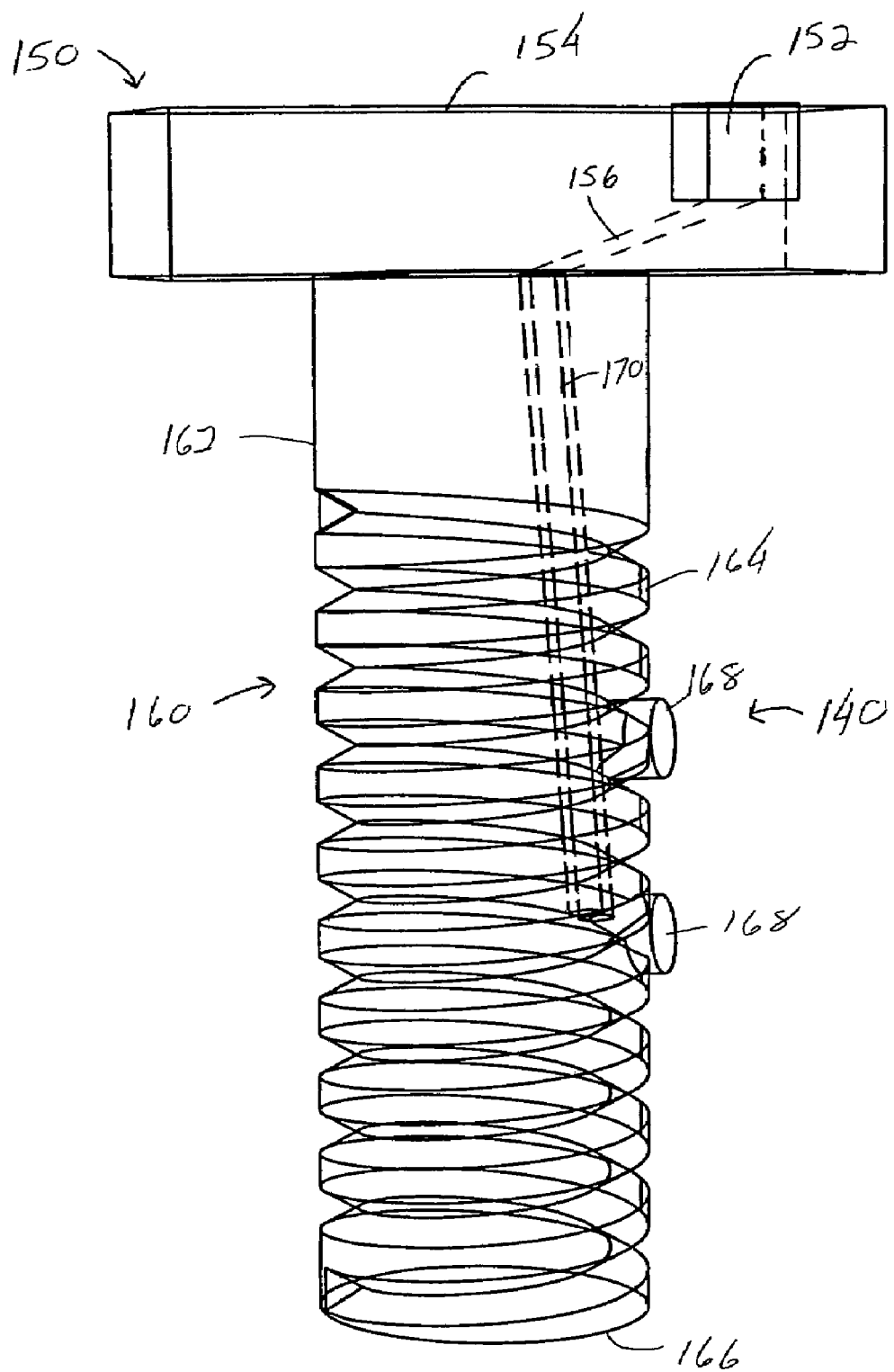
FIG. 8 is still another perspective view of the front side pedicle screw of the present invention which includes an electrical mechanism positioned in the top of the pedicle screw; and, FIG. 9 is yet another perspective view of the front side pedicle screw of the present invention which includes an electrical mechanism and a pump mechanism positioned in the top of the pedicle screw.

Referring now to FIG. 8, still another embodiment of the invention is illustrated. Pedicle screw 140 includes a head 150 and a lower portion 160. The cross-section of head 150 illustrates that the head includes a battery 152 positioned in top surface 154. The battery is illustrated as having an cubical shape; however, other shapes can be used. The head has a rectangular shape; however, other shapes can be used. The battery can be connected in the head in a variety of manners. The battery can also be connected such that the battery can be periodically replaced. A channel 156 is positioned under the battery and travels between the battery and lower portion 160 of the pedicle screw. Typically a wire or other electrical conductor is positioned in the channel. The discharge rate, the discharge duration, etc. of the battery can be constant or electronically controlled.

The lower portion 160 of the pedicle screw includes an outer surface 162 that includes thread 164. The cross-sectional shape of the lower portion is substantially circular and has a substantially constant cross-sectional shape and cross-sectional area throughout the majority of the longitudinal length of the lower portion. The end 166 of the lower portion is substantially flat. As can be appreciated, many other shapes and/or configurations of the head and/or lower portion can be used for the pedicle screw. The lower portion also includes two electrodes 168. As can be appreciated, more electrodes can be located in the lower portion. Furthermore, it can be appreciated that one or more electrodes can be located in the top portion of the pedicle screw. The electrodes are designed to conduct current between the electrodes and to the surrounding tissue. The lower portion also includes one or more channels 170 wherein an electrical conductor is positioned. Channel 170 enables an electrical conductor to connect the electrodes 168 to the electrical conductor in channel 156. The electrodes can be positioned on the same side of the pedicle screw as illustrated in FIG. 8, or positioned on the lower portion in other manners.

Figure 9:
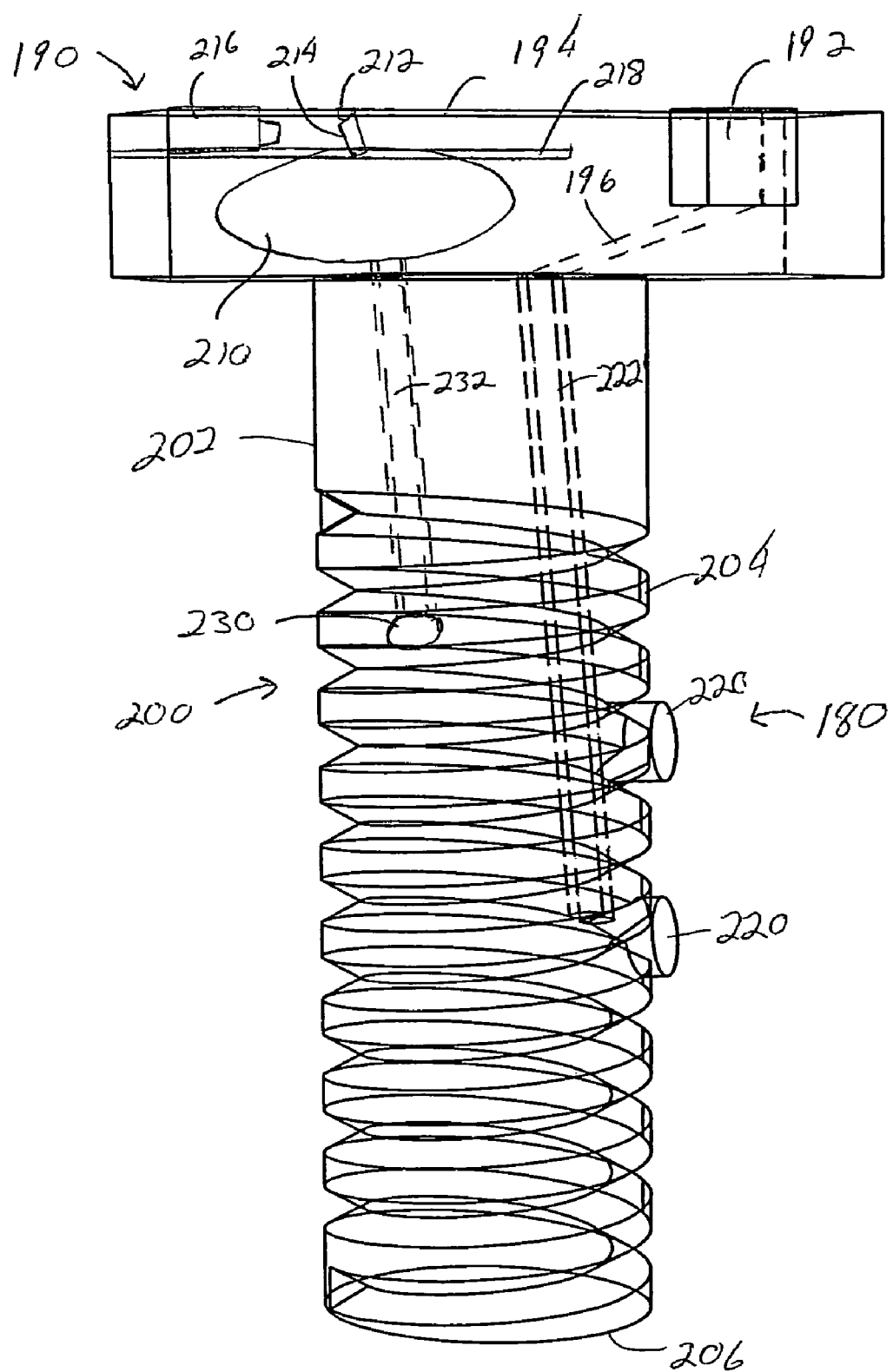

Referring now to FIG. 9, still yet another embodiment of the invention is illustrated. Pedicle screw 180 includes a head 190 and a lower portion 200. The cross-section of head 190 illustrates that the head includes a battery 192 positioned in top surface 194. The battery configuration is similar to that of FIG. 8. As explained with respect the pedicle screw in FIG. 8, the battery can be connected in the head in a variety of manners. The battery can also be connected such that the battery can be periodically replaced. A channel 196 is positioned under the battery and travels between the battery and lower portion 200 of the pedicle screw. Typically a wire or other electrical conductor is positioned in the channel. The discharge rate, the discharge duration, etc. of the battery can be constant or electronically controlled. The cross-section of head 190 also includes one or more reservoirs 210 for containing one or more substances described above. The reservoir is illustrated as having an ovoid shape; however, as explained with respect to FIG. 5, other shapes can be used. The top of head 190 includes one or more port openings 212 to allow one or more substances to be inserted and/or removed from the reservoir. One or more port passages 214 allows fluid passage between port opening 212 and reservoir 210. The port opening can be designed similar to the port opening described with respect to FIG. 5. One or more motors 216 are positioned in head 190. The motor design, type and configuration can be similar to the motor disclosed in FIG. 5. The head also includes one or more pressure plates 218 designed to be moved by the motor to cause the one or more substances in the reservoir to flow out of the reservoir. One or more discharge ports 220 allow one or more substances to flow from the reservoir. The lower portion 200 of the pedicle screw includes an outer surface 202 that includes thread 204. The cross-sectional shape of the lower portion is substantially circular and has a substantially constant cross-sectional shape and cross-sectional area throughout the majority of the longitudinal length of the lower portion. The end 206 of the lower portion is substantially flat. As can be appreciated, many other shapes and/or configurations of the head and/or lower portion can be used for the pedicle screw. The lower portion also includes two electrodes 220. As can be appreciated, more electrodes can be located in the lower portion. Furthermore, it can be appreciated that one or more electrodes can be located in the top portion of the pedicle screw. The electrodes are designed to conduct current between the electrodes and to the surrounding tissue. The lower portion also includes one or more channels 222 wherein an electrical conductor is positioned. Channel 222 enables an electrical conductor to connect the electrodes 220 to the electrical conductor in channel 196. The electrodes can be positioned on the same side of the pedicle screw as illustrated in FIG. 8, or positioned on the lower portion in other manners. The lower portion 200 of the pedicle screw also includes an opening 230. As can be appreciated, more or less openings can be located in the lower portion. Furthermore, it can be appreciated that one or more openings can be located in the top portion of the pedicle screw. The opening is designed to allow at least a portion of the one or more substances to flow out of the opening and to the surrounding bone and/or cartilage. The lower portion also includes one or more channels 232 to allow the one or more substances to flow from the reservoir and out through opening 230. The operation of the motor to cause the one or more substances to flow out through opening 230 can be similar to the manner discussed with respect to FIG. 5.

As stated above, once the pedicle screw is connected to the bone and/or cartilage, the electrical mechanism can be activated so that the battery conducts a current between the electrodes. The electrical mechanism alternatively can be activated prior to complete insertion of the pedicle screw into the bone and/or cartilage. The activation of the electrical mechanism can be manual and/or by a preprogrammed activation mechanism. The discharge rate at which the battery conducts current between the electrodes can be constant or be manually and/or electronically regulated to vary over time.

The invention has been described with reference to the preferred embodiments. These and other modifications of the preferred embodiments as well as other embodiments of the invention will be obvious from the disclosure herein, whereby the foregoing descriptive matter is to be interpreted merely as illustrative of the invention and not as a limitation. It is intended to include all such modifications and alterations insofar as they come within the scope of the appended claims.

I claim:

1. A bone implant in the form of a screw, nail or post for at least partial insertion into a bone and/or cartilage of a spine of a human or animal comprising a head and a lower portion connected to the head, and an electrical mechanism secured to said screw, nail or post, said electrical mechanism designed to promote healing about said bone implant, said lower portion having an outer surface that is designed to directly engage and at least partially penetrate into the bone and/or cartilage of the spine, said outer surface of said lower portion including a plurality of electrical contacts, said plurality of electrical contacts designed to discharge current in or adjacent to the bone and/or cartilage of the spine to promote healing about said bone implant, said electrical mechanism including a self contained current source and an electronic controller, said electronic controller designed to at least partially control a duration, a time, a degree, a sequence or combinations thereof of current flow from said self contained current source into or adjacent to said bone and/or cartilage of the spine.

2. The bone implant as defined in claim 1, wherein said head includes at least a portion of said electrical mechanism.

3. The bone implant as defined in claim 2, wherein said lower portion includes at least a portion of said electrical mechanism.

4. The bone implant as defined in claim 3, wherein at least a portion of said electrical mechanism is releasably connected to said head.

5. The bone implant as defined in claim 2, wherein at least a portion of said electrical mechanism is releasably connected to said head.

6. The bone implant as defined in claim 5, wherein said electronic controller includes a microchip controller, a MEMS controller or combinations thereof.

7. The bone implant as defined in claim 6, wherein said electronic controller includes a programmable device.

8. The bone implant as defined in claim 7, wherein said electronic controller includes a transmitter to transmit a signal to a remote location, a receiver to receive a signal from a remote location, or combinations thereof, said signal including a signal to at least partially recharge said electrical mechanism, to provide instructions and/or programming to said electronic controller, or combinations thereof.

9. The bone implant as defined in claim 8, wherein said receiver of said electronic controller is designed to receive information, said electronic controller designed to be at least partially controlled by said received information, said received information including information selected from the group consisting of data, source code or combinations thereof, said received information adapted to change one or more settings of said electronic controller so as to change said duration, said time, said degree, said sequence or combinations thereof of current flow from said self contained current source into or adjacent to said bone and/or cartilage of the spine.

10. The bone implant as defined in claim 9, wherein said receiver of said electronic controller is designed to receive information to activate said electronic controller, deactivate said electronic controller, or combinations thereof.

11. The bone implant as defined in claim 2, wherein said electronic controller includes a microchip controller, a MEMS controller or combinations thereof.

12. The bone implant as defined in claim 11, wherein said electronic controller includes a programmable device.

13. The bone implant as defined in claim 12, wherein said electronic controller includes a transmitter to transmit a signal to a remote location, a receiver to receive a signal from a remote location, or combinations thereof, said signal including a signal to at least partially recharge said electrical mechanism, to provide instructions and/or programming to said electronic controller, or combinations thereof.

14. The bone implant as defined in claim 13, wherein said receiver of said electronic controller is designed to receive information, said electronic controller designed to be at least partially controlled by said received information, said received information including information selected from the group consisting of data, source code or combinations thereof, said received information adapted to change one or more settings of said electronic controller so as to change said duration, said time, said degree, said sequence or combinations thereof of current flow from said self contained current source into or adjacent to said bone and/or cartilage of the spine.

15. The bone implant as defined in claim 14, wherein said receiver of said electronic controller is designed to receive information to activate said electronic controller, deactivate said electronic controller, or combinations thereof.

16. The bone implant as defined in claim 14, wherein said head, said lower portion or combinations thereof includes at least one cavity containing medical substance, said lower portion including an internal fluid channel fluidly connected to said cavity and at least one opening fluidly connected to said internal fluid channel, said at least one opening allowing said medical substance in said internal channel to be at least partially discharged to or adjacent to the bone and/or cartilage of the spine.

17. The bone implant as defined in claim 16, including a mechanical mechanism that promotes medical substance in said cavity to flow into said internal fluid channel of said lower portion.

18. The bone implant as defined in claim 17, wherein said at least one mechanical mechanism includes a microchip controller, MEMS controller or combinations thereof to at least partially control a flow rate of medical substance, a type of medical substance, or combinations thereof flowing through at least one of said openings.

19. The bone implant as defined in claim 1, wherein said lower portion includes at least a portion of said electrical mechanism.

20. The bone implant as defined in claim 19, wherein said electronic controller includes a microchip controller, a MEMS controller or combinations thereof.

21. The bone implant as defined in claim 20, wherein said electronic controller includes a programmable device.

22. The bone implant as defined in claim 21, wherein said electronic controller includes a transmitter to transmit a signal to a remote location, a receiver to receive a signal from a remote location, or combinations thereof, said signal including a signal to at least partially recharge said electrical mechanism, to provide instructions and/or programming to said electronic controller, or combinations thereof.

23. The bone implant as defined in claim 22, wherein said receiver of said electronic controller is designed to receive information, said electronic controller designed to be at least partially controlled by said received information, said received information including information selected from the group consisting of data, source code or combinations thereof, said received information adapted to change one or more settings of said electronic controller so as to change said duration, said time, said degree, said sequence or combinations thereof of current flow from said self contained current source into or adjacent to said bone and/or cartilage of the spine.

24. The bone implant as defined in claim 23, wherein said receiver of said electronic controller is designed to receive information to activate said electronic controller, deactivate said electronic controller, or combinations thereof.

25. The bone implant as defined in claim 1, wherein said self contained current source includes a battery, an electric generator or combinations thereof.

26. The bone implant as defined in claim 1, wherein said electronic controller includes a microchip controller, a MEMS controller or combinations thereof.

27. The bone implant as defined in claim 26, wherein said electronic controller includes a programmable device.

28. The bone implant as defined in claim 27, wherein said electronic controller includes a transmitter to transmit a signal to a remote location, a receiver to receive a signal from a remote location, or combinations thereof, said signal including a signal to at least partially recharge said electrical mechanism, to provide instructions and/or programming to said electronic controller, or combinations thereof.

29. The bone implant as defined in claim 28, wherein said receiver of said electronic controller is designed to receive information, said electronic controller designed to be at least partially controlled by said received information, said received information including information selected from the group consisting of data, source code or combinations thereof, said received information adapted to change one or more settings of said electronic controller so as to change said duration, said time, said degree, said sequence or combinations thereof of current flow from said self contained current source into or adjacent to said bone and/or cartilage of the spine.

30. The bone implant as defined in claim 29, wherein said receiver of said electronic controller is designed to receive information to activate said electronic controller, deactivate said electronic controller, or combinations thereof.

31. The bone implant as defined in claim 29, wherein said head, said lower portion, or combinations thereof, includes at least one cavity containing medical substance, said lower portion including an internal fluid channel fluidly connected to said cavity and at least one opening fluidly connected to said internal fluid channel, said at least one opening allowing said medical substance in said internal channel to be at least partially discharged to or adjacent to the bone and/or cartilage of the spine.

32. The bone implant as defined in claim 31, including a mechanical mechanism that promotes medical substance in said cavity to flow into said internal fluid channel of said lower portion.

33. The bone implant as defined in claim 32, wherein said at least one mechanical mechanism includes a microchip controller, MEMS controller or combinations thereof to at least partially control a flow rate of medical substance, a type of medical substance, or combinations thereof flowing through at least one of said openings.

34. The bone implant as defined in claim 1, wherein said electronic controller includes a transmitter to transmit a signal to a remote location, a receiver to receive a signal from a remote location, or combinations thereof, said signal including a signal to at least partially recharge said electrical mechanism, to provide instructions and/or programming to said electronic controller, or combinations thereof.

35. The bone implant as defined in claim 34, wherein said receiver of said electronic controller is designed to receive information to activate said electronic controller, deactivate said electronic controller, or combinations thereof.

36. The bone implant as defined in claim 34, wherein said receiver of said electronic controller is designed to receive information, said electronic controller designed to be at least partially controlled by said received information, said received information including information selected from the group consisting of data, source code or combinations thereof, said received information adapted to change one or more settings of said electronic controller so as to change said duration, said time, said degree, said sequence or combinations thereof of current flow from said self contained current source into or adjacent to said bone and/or cartilage of the spine.

37. The bone implant as defined in claim 36, wherein said receiver of said electronic controller is designed to receive information to activate said electronic controller, deactivate said electronic controller, or combinations thereof.

38. The bone implant as defined in claim 36, wherein said head, said lower portion, or combinations thereof, includes at least one cavity containing medical substance, said lower portion including an internal fluid channel fluidly connected to said cavity and at least one opening fluidly connected to said internal fluid channel, said at least one opening allowing said medical substance in said internal channel to be at least partially discharged to or adjacent to the bone and/or cartilage of the spine.

39. The bone implant as defined in claim 19, including a mechanical mechanism that promotes medical substance in said cavity to flow into said internal fluid channel of said lower portion.

40. The bone implant as defined in claim 39, wherein said at least one mechanical mechanism includes a microchip controller, MEMS controller or combinations thereof to at least partially control a flow rate of medical substance, a type of medical substance, or combinations thereof flowing through at least one of said openings.

41. The bone implant as defined in claim 1, wherein said head, said lower portion, or combinations thereof, includes at least one cavity containing medical substance, said lower portion including an internal fluid channel fluidly connected to said cavity and at least one opening fluidly connected to said internal fluid channel, said at least one opening allowing said medical substance in said internal channel to be at least partially discharged to or adjacent to the bone and/or cartilage of the spine.

42. The bone implant as defined in claim 41, including a mechanical mechanism that promotes medical substance in said cavity to flow into said internal fluid channel of said lower portion.

43. The bone implant as defined in claim 42, wherein said mechanical mechanism is detachably connected to said head.

44. The bone implant as defined in claim 42, wherein said mechanical mechanism includes a pump.

45. The bone implant as defined in claim 42, wherein said at least one mechanical mechanism includes a microchip controller, MEMS controller or combinations thereof to at least partially control a flow rate of medical substance, a type of medical substance, or combinations thereof flowing through at least one of said openings.

46. The bone implant as defined in claim 45, wherein said mechanical mechanism includes a transmitter to transmit information to a remote location, a receiver to receive information from a remote location, or combinations thereof.

47. The bone implant as defined in claim 46, wherein said receiver is designed to receive information including information selected from the group consisting of data, source code, or combinations thereof, said received information adapted to change one or more settings of said mechanical mechanism so as to change said flow rate of medical substance, said type of medical substance, or combinations thereof flowing through at least one of said openings.

48. The bone implant as defined in claim 1, wherein said head and/or lower portion at least partially includes a coating material, said coating material including a compound that facilitates in the insertion and/or securing of the lower portion in said bone and/or cartilage of the spine, promotes and/or inhibits bone and/or other tissue growth of the spine, inhibits rejection of said bone implant, inhibits rejection of components connected to and/or located adjacent to said bone implant, reduces infection, reduces inflammation, reduces pain, promotes healing of surrounding tissue of the spine, combats cancer and/or other diseases, combats biological abnormalities, functions as a location and/or visual indicator or combinations thereof.

49. A bone implant in the form of a screw for at least partial insertion into a bone and/or cartilage of the backbone of a human or animal for use in anchoring and/or affixing a second implant to the bone and/or cartilage, said implant comprising a head and a lower portion connected to the head, said lower portion having an outer surface that is designed to directly engage and at least partially penetrate into the bone and/or cartilage, said outer surface of said lower portion including a plurality of electrical contacts, a majority of said outer surface of said lower portion including a threaded surface to facilitate in securing said lower portion to the bone and/or cartilage, said lower portion having a tapered end, said lower portion, head or combination thereof including at least one cavity, said cavity designed to at least partially include at least one electrical mechanism secured to said screw, said electrical mechanism designed to promote healing about said bone implant, said electrical mechanism designed to discharge a current to said bone and/or tissue positioned at least closely adjacent to said implant, said electrical mechanism including a self contained current source and electronic controller designed to at least partially control a duration, a time, a degree or combinations thereof of current flow from said self contained current source into or adjacent to said bone and/or cartilage, said electronic controller including a microchip controller, a MEMS controller or combinations thereof.

50. The bone implant as defined in claim 49, wherein said electronic controller includes a programmable device.

51. The bone implant as defined in claim 50, wherein said head, said lower portion or combinations thereof includes at least one cavity containing medical substance, said lower portion including an internal fluid channel fluidly connected to said cavity and at least one opening fluidly connected to said internal fluid channel, said at least one opening allowing said medical substance in said internal channel to be at least partially discharged to or adjacent to the bone and/or cartilage.

52. The bone implant as defined in claim 51, including a mechanical mechanism that promotes medical substance in said cavity to flow into said internal fluid channel of said lower portion.

53. The bone implant as defined in claim 52, wherein said at least one mechanical mechanism includes a microchip controller, MEMS controller or combinations thereof to at least partially control a flow rate of medical substance, a type of medical substance, or combinations thereof flowing through at least one of said openings.

54. The bone implant as defined in claim 50, wherein said electronic controller includes a transmitter to transmit a signal to a remote location, a receiver to receive a signal from a remote location, or combinations thereof, said signal including a signal to at least partially recharge said electrical mechanism, to provide instructions and/or programming to said electronic controller, or combinations thereof.

55. The bone implant as defined in claim 54, wherein said receiver of said electronic controller is designed to receive information to activate said electronic controller, deactivate said electronic controller, or combinations thereof.

56. The bone implant as defined in claim 54, wherein said receiver of said electronic controller is designed to receive information, said electronic controller designed to be at least partially controlled by said received information, said received information including information selected from the group consisting of data, source code or combinations thereof, said received information adapted to change one or more settings of said electronic controller so as to change said duration, said time, said degree, said sequence or combinations thereof of current flow from said self contained current source into or adjacent to said bone and/or cartilage.

57. The bone implant as defined in claim 56, wherein said receiver of said electronic controller designed to receive information to activate said electronic controller, deactivate said electronic controller, or combinations thereof.

58. The bone implant as defined in claim 57, wherein said head, said lower portion or combinations thereof includes at least one cavity containing medical substance, said lower portion including an internal fluid channel fluidly connected to said cavity and at least one opening fluidly connected to said internal fluid channel, said at least one opening allowing said medical substance in said internal channel to be at least partially discharged to or adjacent to the bone and/or cartilage.

59. The bone implant as defined in claim 58, including a mechanical mechanism that promotes medical substance in said cavity to flow into said internal fluid channel of said lower portion.

60. The bone implant as defined in claim 59, wherein said mechanical mechanism includes a pump.

61. The bone implant as defined in claim 60, wherein said at least one mechanical mechanism includes a microchip controller, MEMS controller, or combinations thereof to at least partially control a flow rate of medical substance, a type of medical substance, or combinations thereof flowing through at least one of said openings.

62. The bone implant as defined in claim 61, wherein said mechanical mechanism includes a transmitter to transmit information to a remote location, a receiver to receive information from a remote location, or combinations thereof.

63. The bone implant as defined in claim 62, wherein said receiver is designed to receive information including information selected from the group consisting of data, source code or combinations thereof, said received information designed to change one or more settings of said mechanical mechanism so as to change said flow rate of medical substance, said type of medical substance, or combinations thereof flowing through at least one of said openings.

64. The bone implant as defined in claim 63, wherein said head and/or lower portion at least partially includes a coating material, said coating material including a compound that facilitates in the insertion and/or securing of the lower portion in said bone and/or cartilage, promotes and/or inhibits bone and/or other tissue growth, inhibits rejection of said bone implant, inhibits rejection of components connected to and/or located adjacent to said bone implant, reduces infection, reduces inflammation, reduces pain, promotes healing of surrounding tissue, combats cancer and/or other diseases, combats biological abnormalities, functions as a location and/or visual indicator or combinations thereof.

65. The bone implant as defined in claim 49, wherein said electronic controller includes a transmitter to transmit a signal to a remote location, a receiver to receive a signal from a remote location, or combinations thereof, said signal including a signal to at least partially recharge said electrical mechanism, to provide instructions and/or programming to said electronic controller, or combinations thereof.

66. The bone implant as defined in claim 65, wherein said head, said lower portion or combinations thereof includes at least one cavity containing medical substance, said lower portion including an internal fluid channel fluidly connected to said cavity and at least one opening fluidly connected to said internal fluid channel, said at least one opening allowing said medical substance in said internal channel to be at least partially discharged to or adjacent to the bone and/or cartilage.

67. The bone implant as defined in claim 66, including a mechanical mechanism that promotes medical substance in said cavity to flow into said internal fluid channel of said lower portion.

68. The bone implant as defined in claim 67, wherein said at least one mechanical mechanism includes a microchip controller, MEMS controller, or combinations thereof to at least partially control a flow rate of medical substance, a type of medical substance, or combinations thereof flowing through at least one of said openings.

69. The bone implant as defined in claim 65, wherein said receiver of said electronic controller is designed to receive information to activate said electronic controller, deactivate said electronic controller, or combinations thereof.

70. The bone implant as defined in claim 10, wherein said receiver of said electronic controller is designed to receive information, said electronic controller designed to be at least partially controlled by said received information, said received information including information selected from the group consisting of data, source code, or combinations thereof, said received information adapted to change one or more settings of said electronic controller so as to change said duration, said time, said degree, said sequence or combinations thereof of current flow from said self contained current source into or adjacent to said bone and/or cartilage.

71. The bone implant connector as defined in claim 70, wherein said receiver of said electronic controller is designed to receive information to activate said electronic controller, deactivate said electronic controller, or combinations thereof.

72. The bone implant as defined in claim 70, wherein said head, said lower portion or combinations thereof includes at least one cavity containing medical substance, said lower portion including an internal fluid channel fluidly connected to said cavity and at least one opening fluidly connected to said internal fluid channel, said at least one opening allowing said medical substance in said internal channel to be at least partially discharged to or adjacent to the bone and/or cartilage.

73. The bone implant as defined in claim 72, including a mechanical mechanism that promotes medical substance in said cavity to flow into said internal fluid channel of said lower portion.

74. The bone implant as defined in claim 73, wherein said at least one mechanical mechanism includes a microchip controller, MEMS controller, or combinations thereof to at least partially control a flow rate of medical substance, a type of medical substance, or combinations thereof flowing through at least one of said openings.

75. The bone implant as defined in claim 49, wherein said head, said lower portion or combinations thereof includes at least one cavity containing medical substance, said lower portion including an internal fluid channel fluidly connected to said cavity and at least one opening fluidly connected to said internal fluid channel, said at least one opening allowing said medical substance in said internal channel to be at least partially discharged to or adjacent to the bone and/or cartilage.

76. The bone implant as defined in claim 75, including a mechanical mechanism that promotes medical substance in said cavity to flow into said internal fluid channel of said lower portion.

77. The bone implant as defined in claim 76, wherein said mechanical mechanism includes a pump.

78. The bone implant as defined in claim 76, wherein said at least one mechanical mechanism includes a microchip controller, MEMS controller or combinations thereof to at least partially control a flow rate of medical substance, a type of medical substance, or combinations thereof flowing through at least one of said openings.

79. The bone implant as defined in claim 78, wherein said mechanical mechanism includes a transmitter to transmit information to a remote location, a receiver to receive information from a remote location, or combinations thereof.

80. The bone implant as defined in claim 79, wherein said receiver is designed to receive information including information selected from the group consisting of data, source code or combinations thereof, said received information adapted to change one or more settings of said mechanical mechanism so as to change said flow rate of medical substance, said type of medical substance, or combinations thereof flowing through at least one of said openings.

81. The bone implant as defined in claim 49, wherein said head and/or lower portion at least partially includes a coating material, said coating material including a compound that facilitates in the insertion and/or securing of the lower portion in said bone and/or cartilage, promotes and/or inhibits bone and/or other tissue growth, inhibits rejection of said bone implant, inhibits rejection of components connected to and/or located adjacent to said bone implant, reduces infection, reduces inflammation, reduces pain, promotes healing of surrounding tissue, combats cancer and/or other diseases, combats biological abnormalities, functions as a location and/or visual indicator or combinations thereof.

82. A bone implant in the form of a screw, nail or post for at least partial insertion into a bone and/or cartilage of a spine of a human or animal comprising a head, a lower portion connected to the head, and an electrical mechanism secured to said screw, nail or post, said electrical mechanism designed to promote healing about said bone implant, said head including at least a portion of said electrical mechanism, said lower portion having an outer surface that is designed to directly engage and at least partially penetrate into the bone and/or cartilage of the spine, said outer surface of said lower portion including a plurality of electrical contacts, said plurality of electrical contacts designed to discharge current in or adjacent to the bone and/or cartilage of the spine to promote healing about said bone implant, said electrical mechanism including a self contained current source and an electronic controller, said electronic controller designed to at least partially control a duration, a time, a degree, a sequence or combinations thereof of current flow from said self contained current source into or adjacent to said bone and/or cartilage of the spine.

83. The bone implant as defined in claim 82, wherein said lower portion includes at least a portion of said electrical mechanism.

84. The bone implant as defined in claim 82, wherein at least a portion of said electrical mechanism is releasably connected to said head.

85. The bone implant as defined in claim 84, wherein said self contained current source includes a battery.

86. The bone implant as defined in claim 85, wherein said electronic controller includes a microchip controller, a MEMS controller or combinations thereof.

87. The bone implant as defined in claim 86, wherein said electronic controller includes a programmable device.

88. The bone implant as defined in claim 87, wherein said electronic controller includes a transmitter to transmit a signal to a remote location, a receiver to receive a signal from a remote location, or combinations thereof said signal including a signal to provide instructions to said electronic controller, provide programming to said electronic controller, provide information about at least a component of said electrical mechanism, or combinations thereof.

89. The bone implant as defined in claim 88, wherein said receiver of said electronic controller is designed to receive information, said electronic controller designed to be at least partially controlled by said received information, said received information including information selected from the group consisting of data, source code or combinations thereof, said received information adapted to change one or more settings of said electronic controller so as to change said duration, said time, said degree, said sequence or combinations thereof of current flow from said self contained current source into or adjacent to said bone and/or cartilage of the spine.

90. The bone implant as defined in claim 89, wherein said receiver of said electronic controller is designed to receive information to activate said electronic controller, deactivate said electronic controller, or combinations thereof.

91. The bone implant as defined in claim 90, wherein said head and/or lower portion at least partially includes a coating material, said coating material including a compound that facilitates in the insertion and/or securing of the lower portion in said bone and/or cartilage of the spine, promotes and/or inhibits bone and/or other tissue growth of the spine, inhibits rejection of said bone implant, inhibits rejection of components connected to and/or located adjacent to said bone implant, reduces infection, reduces inflammation, reduces pain, promotes healing of surrounding tissue of the spine, combats cancer and/or other diseases, combats biological abnormalities, functions as a location and/or visual indicator or combinations thereof.

92. The bone implant as defined in claim 82, wherein said self contained current source includes a battery.

93. The bone implant as defined in claim 82, wherein said electronic controller includes a microchip controller, a MEMS controller or combinations thereof.

94. The bone implant as defined in claim 82, wherein said electronic controller includes a programmable device.

95. The bone implant as defined in claim 82, wherein said electronic controller includes a transmitter to transmit a signal to a remote location, a receiver to receive a signal from a remote location, or combinations thereof, said signal including a signal to provide instructions to said electronic controller, provide programming to said electronic controller, provide information about at least a component of said electrical mechanism, or combinations thereof.

96. The bone implant as defined in claim 95, wherein said receiver of said electronic controller is designed to receive information, said electronic controller designed to be at least partially controlled by said received information, said received information including information selected from the group consisting of data, source code or combinations thereof, said received information adapted to change one or more settings of said electronic controller so as to change said duration, said time, said degree, said sequence or combinations thereof of current flow from said self contained current source into or adjacent to said bone and/or cartilage of the spine.

97. The bone implant as defined in claim 95, wherein said receiver of said electronic controller is designed to receive information to activate said electronic controller, deactivate said electronic controller, or combinations thereof.

98. The bone implant as defined in claim 82, wherein said head and/or lower portion at least partially includes a coating material, said coating material including a compound that facilitates in the insertion and/or securing of the lower portion in said bone and/or cartilage of the spine, promotes and/or inhibits bone and/or other tissue growth of the spine, inhibits rejection of said bone implant, inhibits rejection of components connected to and/or located adjacent to said bone implant, reduces infection, reduces inflammation, reduces pain, promotes healing of surrounding tissue of the spine, combats cancer and/or other diseases, combats biological abnormalities, functions as a location and/or visual indicator or combinations thereof.

* * * * *